US011078511B2

(12) United States Patent
Sobek et al.

(10) Patent No.: US 11,078,511 B2
(45) Date of Patent: Aug. 3, 2021

(54) AQUEOUS COMPOSITION

(71) Applicant: Roche Diagnostics Operations, Inc., Indianapolis, IN (US)

(72) Inventors: Harald Sobek, Biberach (DE); Michael Greif, Penzberg (DE); Marco Thomann, Penzberg (DE); Sebastian Malik, Antdorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/629,040

(22) Filed: Jun. 21, 2017

(65) Prior Publication Data
US 2017/0298405 A1 Oct. 19, 2017

Related U.S. Application Data

(63) Continuation of application No. PCT/EP2015/080741, filed on Dec. 21, 2015.

(51) Int. Cl.
*C12N 9/96* (2006.01)
*C12P 21/00* (2006.01)
*C12N 9/10* (2006.01)
*C12P 19/44* (2006.01)
*C07K 16/00* (2006.01)

(52) U.S. Cl.
CPC ............ *C12P 21/005* (2013.01); *C07K 16/00* (2013.01); *C12N 9/1081* (2013.01); *C12P 19/44* (2013.01); *C12Y 204/99001* (2013.01); *C12Y 301/03* (2013.01); *C07K 2317/41* (2013.01)

(58) Field of Classification Search
None
See application file for complete search history.

(56) References Cited

U.S. PATENT DOCUMENTS

| | | | | |
|---|---|---|---|---|
| 7,892,730 B2 * | 2/2011 | Morris | ................... | C07K 14/47 435/4 |
| 2005/0208496 A1 * | 9/2005 | Ohtani | ................. | C12Q 1/6809 435/6.18 |

FOREIGN PATENT DOCUMENTS

| | | |
|---|---|---|
| WO | 2005/076013 A2 | 8/2005 |
| WO | 2006/112253 A2 | 10/2006 |
| WO | 2007/130638 A2 | 11/2007 |
| WO | 2008/083150 A2 | 7/2008 |
| WO | 2012/113863 A1 | 8/2012 |
| WO | 2012/121041 A1 | 9/2012 |
| WO | 2014/191240 A1 | 12/2014 |

OTHER PUBLICATIONS

Barb, Adam W., et al., Branch-Specific Sialylation of IgG-Fc Glycans by ST6Gal-I, Biochemistry, 2009, pp. 9705-9707, vol. 48.
Chung, Seung-Wook et al., Galactosylation and sialylation of terminal glycan residues of human immunoglobulin G using bacterial glycosyltransferases with in situ regeneration of sugar-nucleotides, Enzyme and Microbial Technology, 2006, pp. 60-66, vol. 39, No. 1.
Donadio, Sandrine et al., Recognition of cell surface acceptors by two human α-2,6-sialyltransferases produced in CHO cells, Biochimie, 2003, pp. 311-321, vol. 85.
International Search Report dated Feb. 25, 2016, in Application No. PCT/EP2015/080741, 5 pages.
Nikonova, E. Yu et al., Specificity of human trans-sialidase as probed with gangliosides, Bioorganic & Medicinal Chemistry Letters, 2004, pp. 5161-5164, vol. 14.
Anderson, J. Christopher et al., An expanded genetic code with a functional quadruplet codon, Proceedings of the National Academy of Sciences USA, 2004, pp. 7566-7571, vol. 101, No. 20.
Bacher, Jamie M. and Ellington, Andrew D., Selection and Characterization of *Escherichia coli* Variants Capable of Growth on an Otherwise Toxic Tryptophan Analogue, Journal of Bacteriology, 2001, pp. 5414-5425, vol. 183, No. 18.
Bork, Kaya et al., Increasing the Sialylation of Therapeutic Glycoproteins: The Potential of the Sialic Acid Biosynthetic Pathway, Journal of Pharmaceutical Sciences, 2009, pp. 3499-3508, vol. 98, No. 10.
Budisa, Nediljko et al., Proteins with β-(thienophrrolyl)alanines as alternative chromophores and pharmaceutically active amino acids, Protein Science, 2001, pp. 1281-1292, vol. 10.
Chin, Jason W. et al., An Expanded Eukaryotic Genetic Code, Science, 2003, pp. 964-967, vol. 301.
Dall'Olio, Fabio, The sialyl-α2, 6-lactosaminyl-structure: Biosynthesis and functional role, Glycoconjugate Journal, 2000, pp. 669-676, vol. 17.
Dalziel, Martin et al., Hepatic acute phase induction of murine β-galactoside α2,6 sialyltransferase (ST6Gal I) is IL-6 dependent and mediated by elevation of Exon H-containing class of transcripts, Glycobiology, 1999, pp. 1003-1008, vol. 9, No. 10.
Hamano-Takaku, Fumie et al., A Mutant *Escherichia coli* Tyrosyl-tRNA Synthetase Utilizes the Unnatural Amino Acid Azatyrosine More Efficiently than Tyrosine, The Journal of Biological Chemistry, 2000, pp. 40324-40328, vol. 275, No. 51.
Ibba, Michael and Söll, Dieter, Genetic Code: Introducing Pyrrolysine, Current Biology, 2002, pp. R464-R466, vol. 12.
Ikeda, Yutaka et al., Synthesis of a novel histidine analogue and its efficient incorporation into a protein in vivo, Protein Engineering, 2003, pp. 699-706, vol. 16, No. 9.
James, D. Andrew et al., Kinetic characterization of ribonuclease S mutants containing photoisomerizable phenylazophenylalanine residues, Protein Engineering, 2001, pp. 983-991, vol. 14, No. 12.

(Continued)

*Primary Examiner* — Hope A Robinson
(74) *Attorney, Agent, or Firm* — Stinson LLP

(57) ABSTRACT

The present disclosure is directed to the properties of certain glycosyltransferase variants having N-terminal truncation deletions or internal deletions. Any of the mutants disclosed in here exhibit alpha-2,6-sialyltransferase enzymatic activity in the presence of CMP-activated sialic acid as co-substrate, and in the presence of a suitable acceptor site. A fundamental finding documented in the present disclosure is that these enzymes are not only capable of catalyzing transfer of a sialidyl moiety but they are also capable of catalyzing hydrolytic cleavage of terminally bound sialic acid from a glycan.

1 Claim, 19 Drawing Sheets

Specification includes a Sequence Listing.

(56) References Cited

OTHER PUBLICATIONS

Kaplan, Howard A. et al., Studies on the Effect of Inflammation on Rat Liver and Serum Sialyltransferase, The Journal of Biological Chemistry, 1983, pp. 11505-11509, vol. 258, No. 15.

Kim, Young S. et al., Properties of a CMP-N-Acetylneuraminic Acid: Glycoprotein Sialyltransferase in Human Serum and Erythrocyte Membranes, Biochimica et Biophysica Acta, 1971, pp. 505-512, vol. 244.

Kleineidam, Reinhard G. et al., Studies on the inhibition of sialyl- and galactosyltransferase, Glycoconjugate Journal, 1997, pp. 57-66, vol. 14.

Kuhn, Bernd et al., The structure of human α-2,6-sialyltransferase reveals the binding mode of complex glycans, Acta Crystallographica Section D, 2013, pp. 1826-1838, vol. 69.

Köhrer, Caroline et al., Import of amber and ochre suppressor tRNAs into mammalian cells: A general approach to site-specific insertion of amino acid analogues into proteins, Proceedings of the National Academy of Sciences USA, 2001, pp. 14310-14315, vol. 98, No. 25.

Patel, Ronak Y. and Balaji, Petery V., Identification of linkage-specific sequence motifs in sialyltransferases, Glycobiology, 2006, pp. 108-116, vol. 16, No. 2.

Stadtman, Thressa C., Selenocysteine, Annual Reviews of Biochemistry, 1996, pp. 83-100, vol. 65.

Van Dijk, M. A. et al., Human antibodies as next generation therapeutics, Current Opinion in Chemical Biology, 2001, pp. 368-374, vol. 5.

Weinstein, Jasminder et al., Primary Structure of β-Galactoside α2,6-Sialyltransferase, The Journal of Biological Chemistry, 1987, pp. 17735-17743, vol. 262, No. 36.

Weinstein, Jasminder et al., Purification of a Galβ1→4GlcNAc α2→6 Sialyltransferase and a Galβ1-→3(4) GlcNAc α2→3 Sialyltransferase to Homogeneity from Rat Liver, The Journal of Biological Chemistry, 1982, pp. 13835-13844, vol. 257, No. 22.

Zhang, Zhiwen et al., Selective incorporation of 5-hydroxytryptophan into proteins in mammalian cells, Proceedings of the National Academy of Sciences USA, 2004, pp. 8882-8887, vol. 101, No. 24.

* cited by examiner

Fig. 1

```
         1    5    10   15   20   25   30   35   40   45   50
Δ57   |xxx|xxxx|xxxx|xxxx|xxxx|xxxx|xxxx|xxxx|xxxx|xxxx|
Δ89   |xxx|xxxx|xxxx|xxxx|xxxx|xxxx|xxxx|xxxx|xxxx|xxxx|
Δ108  |xxx|xxxx|xxxx|xxxx|xxxx|xxxx|xxxx|xxxx|xxxx|xxxx|
WT    MIHTNLKKKFSCCVLVFLLFAVICVWKEKKKGSYYDSFKLQTKEFQVLKS 1   55   60   65   70   75   80   85   90   95  100
Δ57   |xxx|xx..|....|....|....|....|....|....|....|....|
Δ89   |xxx|xxxx|xxxx|xxxx|xxxx|xxxx|xxxx|xxxx|....|....|
Δ108  |xxx|xxxx|xxxx|xxxx|xxxx|xxxx|xxxx|xxxx|xxxx|xxxx|
WT    LGKLAMGSDSQSVSSSSTQDPHRGRQTLGSLRGLAKAKPEASFQVWNKDS 1    5    10   15   20   25   30   35   40   45   50
Δ108  |xxx|xxx.|....|....|....|....|....|....|....|....|
WT    SSKNLIPRLQKIWKNYLSMNKYKVSYKGPGPGIKFSAEALRCHLRDHVNV 1   55   60   65   70   75   80   85   90   95  200
      |...|....|....|....|....|....|....|....|....|....|
WT    SMVEVTDFPFNTSEWEGYLPKESIRTKAGPWGRCAVVSSAGSLKSSQLGR 1    5    10   15   20   25   30   35   40   45   50
      |...|....|....|....|....|....|....|....|....|....|
WT    EIDDHDAVLRFNGAPTANFQQDVGTKTTIRLMNSQLVTTEKRFLKDSLYN 1   55   60   65   70   75   80   85   90   95  300
      |...|....|....|....|....|....|....|....|....|....|
WT    EGILIVWDPSVYHSDIPKWYQNPDYNFFNNYKTYRKLHPNQPFYILKPQM 1    5    10   15   20   25   30   35   40   45   50
      |...|....|....|....|....|....|....|....|....|....|
WT    PWELWDILQEISPEEIQPNPPSSGMLGIIIMMTLCDQVDIYEFLPSKRKT 1   55   60   65   70   75   80   85   90   95  400
      |...|....|....|....|....|....|....|....|....|....|
WT    DVCYYYQKFFDSACTMGAYHPLLYEKNLVKHLNQGTDEDIYLLGKATLPG 1    5
      |...|.
      FRTIHC
```

AQUEOUS COMPOSITION

CROSS-REFERENCE TO RELATED APPLICATIONS

This application is a continuation of International Application No. PCT/EP2015/080741 filed Dec. 21, 2015, claiming priority to European Application No. 141996481.8 filed Dec. 22, 2014, the disclosures of which are hereby incorporated by reference in their entirety.

BACKGROUND

The present disclosure is directed to the properties of certain glycosyltransferase variants having N-terminal truncation deletions or internal deletions. Any of the mutants disclosed in here exhibit α-2,6-sialyltransferase enzymatic activity in the presence of CMP-activated sialic acid as co-substrate, and in the presence of a suitable acceptor site. A fundamental finding documented in the present disclosure is that such enzymes are not only capable of catalyzing transfer of a sialidyl moiety but they are also capable of catalyzing hydrolytic cleavage of terminally bound sialic acid from a glycan. Particularly it was found that in the presence of cytidine-5'-monophosphate (CMP) glycosyltransferase activity is inhibited, and sialidase activity is stimulated. Sialidase activity was found to be dependent on the presence of a particular stretch of amino acids (position 90 to 108) in the polypeptide sequence of the reference (wildtype) hST6Gal-I polypeptide. Deletion of this sequence portion in an N-terminal truncation variant was found to abolish sialidase activity, notably both in the presence and in the absence of CMP. Thus, disclosed are compositions, uses and methods employing the CMP-mediated feed-back regulation documented herein.

Contrary to previous findings α-2,6-sialyltransferase mutants were found to exhibit sialidase enzymatic activity, particularly (but not limited to) a variant of human β-galactoside-α-2,6-sialyltransferase I (hST6Gal-I; wildtype amino acid sequence see SEQ ID NO:1) with a truncation deletion involving the first 89 N-terminal amino acids of the respective wild-type polypeptide (i.e. a mutant with the amino acid sequence of SEQ ID NO:2). A fundamental finding documented in the present disclosure is that this mutant enzyme is not only capable of catalyzing transfer of a sialidyl moiety; in fact, the α-2,6-sialyltransferase variant is also capable of catalyzing hydrolytic cleavage of terminally bound sialic acid from a glycan. The present disclosure further reports the unexpected observation of feed-back inhibition. Particularly it was found that in the presence of cytidine-5'-monophosphate (CMP) glycosyltransferase activity is inhibited, and sialidase activity is stimulated. Even more surprising, not only the deletion mutant involving the first 89 N-terminal amino acids but also other N-terminal truncation variants of human β-galactoside-α-2,6-sialyltransferase I (hST6Gal-I) were found to exhibit sialidase enzymatic activity. However, sialidase activity was found to be dependent on the presence of a particular stretch of amino acids (position 90 to 108, see FIG. 1) in the polypeptide sequence of the reference (wildtype) hST6Gal-I polypeptide according to SEQ ID NO: 1. Deletion of this sequence portion in an N-terminal truncation variant was found to abolish sialidase activity, notably both in the presence and in the absence of CMP. Thus, disclosed are compositions, uses and methods employing the CMP-mediated feed-back regulation documented herein, particularly directed to controlled hydrolysis of the α2,6 glycosidic bond in a N-acetylneuraminyl-α2,6-β-D-galactosyl-1,4-N-acetyl-β-D-glucosamine moiety. Further, compositions, uses and methods with a CMP-insensitive hST6Gal-I are disclosed.

Transferases (EC 2) catalyze transfer of a functional group from one substance to another. Glycosyltransferases, a superfamily of enzymes, are involved in synthesizing the carbohydrate portions of glycoproteins, glycolipids and glycosaminoglycans. Specific glycosyltransferases synthesize oligosaccharides by the sequential transfer of the monosaccharide moiety of an activated sugar donor to an acceptor molecule. Hence, a "glycosyltransferase" catalyzes the transfer of a sugar moiety from its nucleotide donor to an acceptor moiety of a polypeptide, lipid, glycoprotein or glycolipid. This process is also known as "glycosylation". A carbohydrate portion which is structural part of e.g. a glycoprotein is also referred to as "glycan". Glycans constitute the most prevalent of all known post-translational protein modifications. Glycans are involved in a wide array of biological recognition processes as diverse as adhesion, immune response, neural cell migration and axonal extension. As structural part of glycoproteins glycans also have a role in protein folding and the support of protein stability and biological activity.

In glycosyltransferase catalysis, the monosaccharide units glucose (Glc), galactose (Gal), N-acetylglucosamine (GlcNAc), N-acetylgalactosamine (GalNAc), glucuronic acid (GlcUA), galacturonic acid (GalUA) and xylose are activated as uridine diphosphate (UDP)-α-D derivatives; arabinose is activated as a UDP-β-L derivative; mannose (Man) and fucose are activated as GDP-α-D and GDP-β-L derivatives, respectively; and sialic acid (=β-D-Neu5Ac; =Neu5Ac; =SA; =NANA) is activated as a CMP derivative of sialic acid. CMP-activated sialic acid (=CMP-β-D-Neu5Ac, see below) appears to be the only naturally occurring nucleotide sugar in the form of a nucleotide monophosphate.

Many different glycosyltransferases contribute to the synthesis of glycans. The structural diversity of carbohydrate portions of glycoproteins is particularly large and is determined by complex biosynthetic pathways. In eukaryotes the post-translational biosynthesis of the glycan-part of glycoproteins takes place in the lumen of the endoplasmatic reticulum ("ER") and the Golgi apparatus. A single (branched or linear) carbohydrate chain of a glycoprotein is typically a N- or an O-linked glycan. During post-translational processing, carbohydrates are typically connected to the polypeptide via asparagine ("N-linked glycosylation"), or via serine or threonine ("O-linked glycosylation"). Synthesis of a glycan, no matter whether N- or O-linked (="N-/O-linked") is effected by the activity of several different membrane-anchored glycosyltransferases. A glycoprotein may comprise one or more glycan-connected amino acids (="glycosylation sites"). A specific glycan structure may be linear or branched. Branching is a notable feature of carbohydrates which is in contrast to the linear nature typical for DNA, RNA, and polypeptides. Combined with the large heterogeneity of their basic building blocks, the monosaccharides, glycan structures exhibit high diversity. Furthermore, in members of a particular glycoprotein species the structure of a glycan attached to a particular glycosylation site may vary, thus resulting in microheterogeneity of the respective glycoprotein species, i.e. in a species sharing the same amino acid sequence of the polypeptide portion.

A sialyltransferase (="ST") is a glycosyltransferase that catalyzes transfer of a sialic acid residue from a donor compound to (i) a terminal monosaccharide acceptor group of a glycolipid or a ganglioside, or (ii) to a terminal monosaccharide acceptor group of an N-/O-linked glycan of a glycoprotein. For the purpose of the present disclosure, the donor compound is also referred to as "co-substrate". For mammalian sialyltransferases including human ST species there is a common donor compound which is cytidine-5'-monophospho-N-acetylneuraminic acid (=CMP-β-D-Neu5Ac=CMP-Neu5Ac=CMP-NANA; =CMP-sialic acid; =CMP-SA). Well known to the skilled person, CMP-sialic acid is a specific embodiment of a donor compound for a sialyltransferase; further, there exist functional equivalents including but not limited to CMP-9-fluoresceinyl-sialic acid. Transfer and covalent coupling of a sialic acid residue (or the functional equivalent thereof) to a receptor site is also referred to as "sialylating" and "sialylation".

In the glycan structure of a sialylated glycoprotein the (one or more) sialyl moiety (moieties) is (are) usually found in the terminal position of an oligosaccharide. Thus, depending on the amount of sialylated sites, one or more sialic acid residue(s) can form part of a glycan moiety of a given glycoprotein. Owing to the terminal, i.e. exposed position, sialic acid can participate in many different biological recognition phenomena and serve in different kinds of biological interactions. In a glycoprotein more than one sialylation site may be present, i.e. a site capable of serving as a substrate for a sialyltransferase and being an acceptor group suitable for the transfer of a sialic acid residue. Such more than one site can in principle be the termini of a plurality of linear glycan portions anchored at different glycosylation sites of the glycoprotein. Additionally, a branched glycan may have a plurality of sites where sialylation can occur.

According to current knowledge, a terminal sialic acid residue can be found (i) α2→3 (α2,3) linked to galactosyl-R, (ii) α2→6 (α2,6) linked to galactosyl-R, (iii) α2→6 (α2,6) linked to N-acetylgalactosaminidyl-R, (iv) α2→6 (α2,6) linked to N-acetylglucosaminidyl-R, and (v) α2→8/9 (α2,8/9) linked to sialidyl-R, wherein -R denotes the rest of the acceptor substrate moiety. Hence, a sialyltransferase active in the biosynthesis of sialylconjugates is generally named and classified according to its respective monosaccharide acceptor substrate and according to the 3, 6 or 8/9 position of the glycosidic bond it catalyzes. Accordingly, in the literature known to the art, e.g. in Patel R Y, et al, Glycobiology 16 (2006) 108-116, reference to eukaryotic sialyltransferases is made such as (i) ST3Gal, (ii) ST6Gal, (iii) ST6GalNAc, or (v) ST8Sia, depending on the hydroxyl position of the acceptor sugar residue to which the Neu5Ac residue is transferred while forming a glycosidic bond. Reference to sialyltransferases in a more generic way can also be made e.g. as ST3, ST6, ST8; thus, "ST6" specifically encompasses the sialyltransferases catalyzing an α2,6 sialylation.

The disaccharide moiety β-D-galactosyl-1,4-N-acetyl-β-D-glucosamine (=Galβ1,4GlcNAc) is a frequent terminal residue of the antennae of N-linked glycans of glycoproteins, but may be also present in O-linked glycans and in glycolipids. In addition, a terminal Galβ1,4GlcNAc moiety can be generated in certain target glycoproteins as a result of galactosyltransferase enzymatic activity. The enzyme β-galactoside-α2,6-sialyltransferase (="ST6Gal") is able to catalyze α2,6-sialylation of a terminal Galβ1,4GlcNAc acceptor moiety of a glycan or a branch of a glycan, also known to the art as "antenna". For general aspects thereof, reference is made to the document of DallOlio F. Glycoconjugate Journal 17 (2000) 669-676. In human and in other mammals there appear to be several species (isozymes) of ST6Gal. The present disclosure particularly discloses human β-galactoside-α-2,6-sialyltransferase I (=hST6Gal-I; EC 2.4.99.1 according to IUBMB Enzyme Nomenclature) and variants thereof, but is not limited thereto.

The ST6 group of sialyltransferases comprises two sub-groups, ST6Gal and ST6GalNAc. The activity of ST6Gal enzymes catalyzes transfer of a Neu5Ac residue to the C6 hydroxyl group of a free galactosyl residue being part of terminal Galβ1,4GlcNAc in a glycan or an antenna of a glycan, thereby forming in the glycan a terminal sialic acid residue α2→6 linked to the galactosyl residue of the Galβ1,4GlcNAc moiety. The resulting newly formed terminal moiety in the glycan is Neu5Acα2,6Galβ1,4GlcNAc.

The wild-type polypeptide of human β-galactoside-α-2,6-sialyltransferase I (hST6Gal-I) at the time of filing of the present document was disclosed as "UniProtKB/Swiss-Prot: P15907.1" in the publically accessible NCBI database (www.ncbi.nlm.nih.gov/protein/115445). Further information including coding sequences are provided as hyperlinks compiled within the database entry "Gene ID: 6480" (www.ncbi.nlm.nih.gov/gene/6480).

Mammalian sialyltransferases share with other mammalian Golgi-resident glycosyltransferases a so-called "type II architecture" with (i) a short cytoplasmic N-terminal tail, (ii) a transmembrane fragment followed by (iii) a stem region of variable length and (iv) a C-terminal catalytic domain facing the lumen of the Golgi apparatus (Donadio S. et al. in Biochimie 85 (2003) 311-321). Accordingly, a "soluble" sialyltransferase with an N-terminal truncation deletion lacks at least the elements (i) and (ii) of the type II architecture. Mammalian sialyltransferases appear to display significant sequence homology in their catalytic domain. Recent data regarding structure and function of hST6Gal-I are disclosed in Kuhn B. et al. (Biol. Crystallography D69 (2013) 1826-1838).

In certain mammals including mouse, rat and humans, ST6Gal has widespread tissue distribution. It is particularly abundant in liver, the major site of serum glycoprotein synthesis (Weinstein J. et al. J. Biol. Chem 257 (1982) 13835-13844). On the one hand sialyltransferase exists predominantly in a membrane-bound form within the Golgi and trans-Golgi network where it participates in the post-translational modification of newly synthesized secretory or cell surface glycoproteins. On the other hand, a soluble form of ST6Gal-I exists in the serum (Kim Y. S. et al. Biochim. Biophys Acta 244 (1971) 505-512; Dalziel M. et al. Glycobiology 9 (1999) 1003-1008) and predominantly is derived from the liver (Kaplan, H. A. et al. J. Biol. Chem. 258 (1983) 11505-11509; van Dijk, W. et al. Biochem. Cell. Biol. 64 (1986) 79-84; Dalziel M. et al. (supra)) by a proteolytic event that liberates the catalytic domain from its membrane anchor (Kaplan et al., supra; Weinstein, J. et al. J. Biol. Chem. 262 (1987) 17735-17743). Thus, any variant of an originally membrane-anchored glycosyltransferase with an N-terminal truncation comprising the membrane anchor is encompassed by the term "soluble variant". Soluble variants can exemplarily be generated by proteolytically removing the portion with the membrane anchor from the protein, or by expressing a variant nucleic acid sequence encoding a N-terminally truncated form of the original protein wherein the truncation includes the membrane anchor (transmembrane fragment, element (ii) of the type II architecture).

Donadio S. et al. (supra) recombinantly expressed several N-terminally truncated variants of hST6Gal-I without the membrane anchor in CHO cells. The authors found that N-terminal deletions comprising the first 35, 48, 60 and 89 amino acids yielded variants of hST6Gal-I which were enzymatically active and capable of transferring sialic acid to exogenous acceptors.

Glycosylation is an important posttranslational modification of proteins influencing protein folding, stability and regulation of the biological activity. The sialyl residue is usually exposed at the terminal position of an N-glycan and therefore, a major contributor to biological recognition and ligand function. As an important example, IgG with glycans featuring terminal sialic acid residues were found to induce reduced inflammatory response and showed an increase in serum half-life. Therefore, use of glycosyltransferases for enzymatic synthesis of defined glycan structures is becoming an engineering tool towards direct in vitro N-glycosylation of therapeutic proteins, and particularly therapeutic monoclonal antibodies.

Since glycosyltransferases of prokaryotic origin usually do not act on complex glycoprotein structures, sialyltransferases of mammalian origin are preferred for in vitro glycoengineering purposes. For example, Barb et al. (2009) prepared highly sialylated forms of the Fc fragment of immunoglobulin G using isolated human ST6Gal-I. However, the access to recombinant hST6Gal-I for such applications is still limited due to low expression yield and/or poor activity of hST6Gal-I recombinantly expressed in various hosts (methylotrophic yeast *Pichia pastoris*, cultured *Spodoptera frugiperda* cells, *E. coli*-based expression systems).

Kleineidam R. G. et al. Glycoconjugate Journal (1997) 14: 57-66 disclose a number of inhibitors of α-2,6-sialyltransferase from rat liver. Specifically, 70%, 40%, 39% and 71% inhibition of α-2,6-sialyltransferase was observed in the presence of Cytidine, 2'-CMP, 3'-CMP and 5'-CMP, respectively, wherein each inhibitor was tested at a concentration of 0.25 mM.

While the use of mammalian glycosyltransferases for in vitro sialylating a glycosylated target molecule such as a glycoprotein or a glycolipid is known to the art, the opposite reaction (sialidase activity, hydrolytic cleavage of a terminal sialyl residue from a glycan moiety) is typically provided by a neuraminidase, so far. The original finding by the present inventors is, however, that a soluble variant of a sialyltransferase of mammalian origin displays sialidase activity in the presence of CMP. In fact, the specific example of a soluble variant of human β-galactoside-α-2,6-sialyltransferase I lacking the transmembrane domain by means of a N-terminal truncation can be used for both, (i) sialylation of a target glycoprotein and (ii) hydrolytic cleavage of sialyl residues from a sialylated target glycoprotein. Depending on the presence of CMP and the interaction of CMP with the soluble variant, sialylation can be controlled quantitatively. In specific embodiments involving target molecules with two or more antennal glycan acceptor sites, the present disclosure provides means, methods and conditions allowing to sialylate just one out of the several acceptor sites, as well as sialylating two or more, or even all acceptor sites of the target molecule.

This paves the way for a number of different approaches, particularly in the field of in vitro glycoengineering of immunoglobulins, and also of other glycosylated target molecules.

SUMMARY

In a first aspect and a specific embodiment of all other aspects as disclosed herein there is disclosed an aqueous composition comprising
(a) a soluble human β-galactoside-α-2,6-sialyltransferase I comprising the amino acid motif from position 90 to position 108 in SEQ ID NO:1;
(b) cytidine-5'-monophospho-N-acetylneuraminic acid, or a functional equivalent thereof;
(c) a glycosylated target molecule selected from a glycoprotein and a glycolipid, the target molecule comprising one or more antenna(e), at least one antenna having as a terminal structure a β-D-galactosyl-1,4-N-acetyl-β-D-glucosamine moiety with a hydroxyl group at the C6 position in the galactosyl residue;
(d) an aqueous solution permitting glycosyltransferase enzymatic activity;
wherein the aqueous composition further comprises an enzyme capable of hydrolyzing the phosphoester bond in 5'-cytidine-monophosphate under conditions permitting glycosyltransferase enzymatic activity.

In a second aspect and a specific embodiment of all other aspects as disclosed herein there is disclosed the use of an enzyme capable of the hydrolyzing phosphoester bond in 5'-cytidine-monophosphate for maintaining sialyltransferase enzymatic activity and/or inhibiting sialidase enzymatic activity in a composition according to the first aspect.

In a third aspect and a specific embodiment of all other aspects as disclosed herein there is disclosed a method of producing in vitro a sialylated target molecule, the method comprising the steps of
(a) providing an aqueous composition according to any of the claims 1 and 2;
(b) forming one or more terminal antennal N-acetylneuraminyl-α2,6β-D-galactosyl-1,4-N-acetyl-β-D-glucosamine residue(s) by incubating the aqueous composition of step (a), thereby reacting cytidine-5'-monophospho-N-acetylneuraminic acid, or a functional equivalent thereof, as co-substrate, thereby forming 5'-cytidine-monophosphate;
(c) hydrolyzing the phosphoester bond of the 5'-cytidine-monophosphate formed in step (b), thereby reducing 5'-cytidine-monophosphate-mediated inhibition, thereby maintaining the activity of the soluble human β-galactoside-α-2,6-sialyltransferase I;
thereby producing in vitro the sialylated target molecule.

In a fourth aspect and a specific embodiment of all other aspects as disclosed herein there is disclosed a preparation of sialylated immunoglobulins, each immunoglobulin having a plurality of acceptor sites for human β-galactoside-α-2,6-sialyltransferase I, wherein less than about 25% of the acceptor sites in the preparation of sialylated immunoglobulins are not sialylated, and about 75% or more are sialylated, wherein the preparation is obtained by a method according to the third aspect.

In a fifth aspect and a specific embodiment of all other aspects as disclosed herein there is disclosed the use of a soluble human β-galactoside-α-2,6-sialyltransferase I comprising the amino acid motif from position 90 to position 108 in SEQ ID NO:1 for in vitro hydrolyzing in the presence of 5'-cytidine-monophosphate the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid.

DESCRIPTION OF THE FIGURES

FIG. 1 Representation of the amino acid sequence of the wild-type hST6Gal-I polypeptide (SEQ ID NO:1), and the N-terminal portions thereof which are truncated in the deletion variants as disclosed herein. The deleted positions in the truncations are symbolized by "X". Underlined are the amino acid at positions 90-108 (SEQ ID NO:1) found to be essential for CMP-induced sialidase activity.

DETAILED DESCRIPTION

Figure 2:
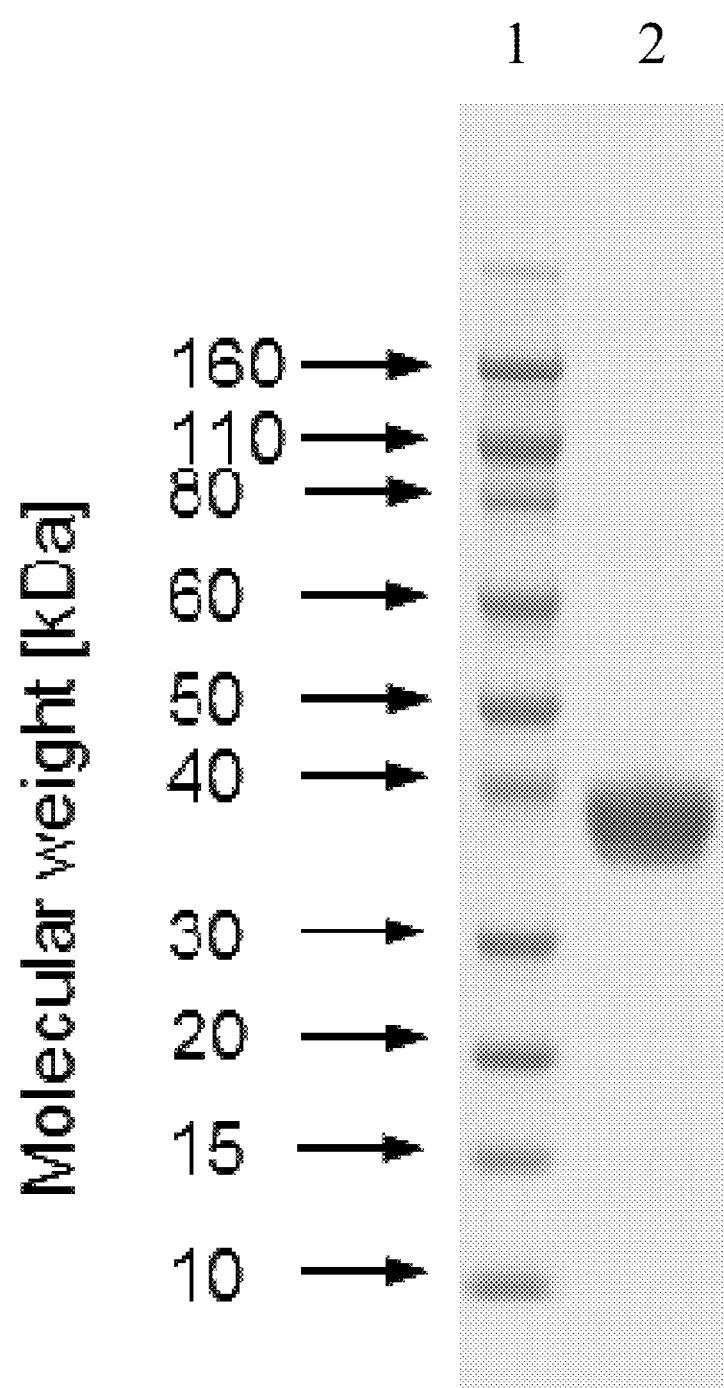
FIG. 2 SDS-PAGE gel after electrophoresis and staining of the Δ89 hST6Gal-I variant transiently expressed in and secreted from HEK cells. Lane 1 shows a size-standard, molecular weights in kDa according to the standard are indicated to the left. Lane 2: Purified Δ89 hST6Gal-I truncation variant (5 µg of protein were loaded on the gel).

The terms "a", "an" and "the" generally include plural referents, i.e. "one or more", unless the context clearly indicates otherwise. As used herein, "plurality" is understood to mean more than one. For example, a plurality refers to at least two, three, four, five, or more. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about".

The term "amino acid" generally refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of Escherichia coli Variants Capable of Growth on an Otherwise Toxic Tryptophan Analogue," J. Bacteriol. 183(18):5414-5425, Hamano-Takaku et al. (2000) "A Mutant Escherichia coli Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7):1281-1292. To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynyl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "protein" refers to a polypeptide chain (amino acid sequence) as a product of the ribosomal translation process, wherein the polypeptide chain has undergone post-translational folding processes resulting in three-dimensional protein structure. The term "protein" also encompasses polypeptides with one or more posttranslational modifications such as (but not limited to) glycosylation, phosphorylation, acetylation and ubiquitination.

Any protein as disclosed herein, particularly recombinantly produced protein as disclosed herein, may in a specific embodiment comprise a "protein tag" which is a peptide sequence genetically grafted onto the recombinant protein. A protein tag may comprise a linker sequence with a specific protease cleavage site to facilitate removal of the tag by proteolysis. As a specific embodiment, an "affinity tag" is appended to a target protein so that the target can be purified from its crude biological source using an affinity technique. For example, the source can be a transformed host organism expressing the target protein or a culture supernatant into which the target protein was secreted by the transformed host organism. Specific embodiments of an affinity tag include chitin binding protein (CBP), maltose binding protein (MBP), and glutathione-S-transferase (GST). The poly(His) tag is a widely-used protein tag which facilitates binding to certain metal chelating matrices.

Each of the terms "chimeric protein", "fusion protein" or "fusion polypeptide" equally refers to a protein whose amino acid sequence represents a fusion product of subsequences of the amino acid sequences from at least two distinct proteins. A fusion protein typically is not produced by direct manipulation of amino acid sequences, but, rather, is expressed from a "chimeric" gene that encodes the chimeric amino acid sequence.

The term "recombinant" refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" or "recombinantly produced protein" is a protein made using recombinant techniques, i.e., through the expression of a recombinant nucleic acid as depicted above.

The term "host cell" refers to both single-cellular prokaryote and eukaryote organisms (e.g., mammalian cells, insect cells, bacteria, yeast, and actinomycetes) and single cells from higher order plants or animals when being grown in cell culture.

The term "glycosylation" denotes the chemical reaction of covalently coupling a glycosyl residue to an acceptor group. One specific acceptor group is a hydroxyl group, e.g. a hydroxyl group of another sugar. "Sialylation" is a specific form of glycosylation wherein the acceptor group is reacted with a sialic acid (=N-acetylneuraminic acid) residue. Such a reaction is typically catalyzed by a sialyltransferase enzyme using cytidine-5'-monophospho-N-acetyl-neuraminic acid as donor compound or co-substrate.

"Sialylation" is a specific embodiment of a result of glycosyltransferase enzymatic activity (sialyltransferase enzymatic activity in the particular case), under conditions permitting the same.

Generally, the skilled person appreciates that the aqueous composition in which glycosyltransferase enzymatic activity can take place (=under conditions "permitting glycosyltransferase enzymatic activity") needs to be buffered using a buffer salt such as Tris, MES, phosphate, acetate, or another buffer salt specifically capable of buffering in the pH range of pH 6 to pH 8, more specifically in the range of pH 6 to pH 7, even more specifically capable of buffering a solution of about pH 6.5. The buffer may further contain a neutral salt such as but not limited to NaCl. Further, in particular embodiments the skilled person may consider adding to the aqueous buffer a salt comprising a divalent cation such as $Mg^{2+}$ or $Mn^{2+}$, e.g., but not limited to, $MgCl_2$ and $MnCl_2$. In additional specific embodiments, the aqueous composition permitting glycosyltransferase enzymatic activity may comprise an antioxidant and/or a surfactant. Conditions permitting glycosyltransferase enzymatic activity known to the art include ambient (room) temperature, but more generally temperatures in the range of 0° C. to 40° C., particularly 10° C. to 30° C., particularly about 20° C. While the above described conditions provide general conditions permitting such enzymatic activity, glycosyltransferase activity further requires the presence of an activated sugar donor (such as specifically CMP-Neu5Ac) as a co-substrate, in addition. However, the term "permitting glycosyltransferase enzymatic activity" is understood as not necessarily including the presence of the co-substrate. Thus, the term "permitting glycosyltransferase enzymatic activity" herein also includes conditions permitting the hydrolysis (sialidase) activity of a mammalian glycosyltransferase subject of the present disclosure, particularly hydrolysis activity in the presence of 5'-cytidine-monophosphate (CMP).

The term "glycan" refers to a poly- or oligosaccharide, i.e. to a multimeric compound which upon acid hydrolysis yields a plurality of monosaccharides. A glycoprotein comprises one or more glycan moieties which are covalently coupled to side groups of the polypeptide chain, typically via asparagine or arginine ("N-linked glycosylation") or via serine or threonine ("O-linked glycosylation").

The use of glycosyltransferases for enzymatic synthesis of complex glycan structures is an attractive approach to obtain complex bioactive glycoproteins. E.g. Barb et al. Biochemistry 48 (2009) 9705-9707 prepared highly potent sialylated forms of the Fc fragment of immunoglobulin G using isolated human ST6Gal-I. However, growing interest in the therapeutic application of glycoproteins leads to an increasing demand of glycosyltransferases including sialyltransferases. Different strategies to increase or modify the sialylation of glycoproteins were described by Bork K. et al. J. Pharm. Sci. 98 (2009) 3499-3508. An attractive strategy is sialylation in vitro of recombinantly produced proteins (such as but not limited to immunoglobulins and growth factors), particularly therapeutic proteins. To this end, several research groups described expression of sialyltransferases in transformed organisms and purification of the recombinantly produced sialyltransferases. As glycosyltransferases of prokaryotic origin usually do not act on complex glycoproteins (e.g. antibodies), sialyltransferases from mammalian origin were studied with preference.

Particular glycoproteins subject to the disclosures and all aspects of the present document and the aspects and embodiments herein comprise without limitation cell surface glycoproteins and glycoproteins present in soluble form in serum ("serum glycoprotein"), the glycoproteins particularly being of mammalian origin. A "cell surface glycoprotein" is understood to be glycoprotein of which a portion is located on and bound to the surface of a membrane, by way of a membrane anchor portion of the surface glycoprotein's polypeptide chain, wherein the membrane is part of a biological cell. The term cell surface glycoprotein also encompasses isolated forms of the cell surface glycoprotein as well as soluble fragments thereof which are separated from the membrane anchor portion, e.g. by proteolytic cleavage or by recombinant production of such soluble fragments. A "serum glycoprotein" is understood as a glycoprotein being present in serum, i.e. a blood protein present in the non-cellular portion of whole blood, e.g. in the supernatant following sedimentation of cellular blood components. Without limitation, a specifically regarded and embodied serum glycoprotein is an immunoglobulin. Particular immunoglobulins mentioned in here belong to the IgG group (characterized by Gamma heavy chains), specifically any of four the IgG subgroups. For the disclosures, aspects and embodiments herein the term "serum glycoprotein also encompasses a monoclonal antibody; monoclonal antibodies artificially are well known to the art and can be produced e.g. by hybridoma cells or recombinantly using transformed host cells. A further serum specific glycoprotein is a carrier protein such as serum albumin, a fetuin, or another glycoprotein member of the superfamily of histidine-rich glycoproteins of which the fetuins are members. Further, without limitation, a specifically regarded and embodied serum glycoprotein regarding all disclosures, aspects and embodiments herein is a glycosylated protein signalling molecule. A particular molecule of this group is erythropoietin (EPO).

For in vitro engineering of glycoproteins glycosyltransferases can be used as an efficient tool (Weijers 2008). Glycosyltransferases of mammalian origin are compatible with glycoproteins as substrates whereas bacterial glycosyltransferases usually modify simpler substrates like oligosaccharides. For this reason synthetic changes in the glycan moieties of glycoproteins are advantageously made using mammalian glycosyltransferases as tools of choice. However, for a large scale application of glycosyltransferases in glycoengineering availability of suitable enzymes in large (i.e. industrial) quantities is required. The disclosure herein particularly provides proteins with (i) hST6Gal-I sialyltransferase activity and (ii) sialidase activity which can be used for quantitatively controlled in vitro sialylation of target glycoproteins with one or more accessible galactosyl substrate moiety/moieties.

Importantly, the amino acid motif in human β-galactoside-α-2,6-sialyltransferase I from position 90 to position 108 in SEQ ID NO:1 is required for the enzyme to be capable of exhibiting sialidase activity. At the same time, this amino acid motif is required for the enzyme to interact with 5'-CMP. Very remarkably a truncation deletion mutant, a soluble human β-galactoside-α-2,6-sialyltransferase I variant lacking the contiguous N-terminal stretch of the amino acids from position 1 to position 108 does not exhibit sialidase activity, not even in the presence of CMP. Thus, it was concluded that the amino acid motif in human β-galactoside-α-2,6-sialyltransferase I from position 90 to position 108 in SEQ ID NO:1 is essential for these properties to be present.

Suitable targets to treat with sialidase activity include on the one hand asialoglycoproteins, i.e. glycoproteins from which sialic acid residues have been removed by the action of sialidases. On the other hand, bi-sialylated glycoproteins may serve as substrate for sialidase activity. Very advantageously, asialo-, mono-sialylated and bi-sialylated immunoglobulins are specific substrates, particularly immunoglobulins of the IgG class.

While expressing wild-type hST6Gal-I in the methylotrophic yeast *Pichia pastoris* and having targeted the expressed polypeptide to the secretory pathway of the host organism, different truncated variants of recombinantly produced hST6Gal-I were observed. Generally, hST6Gal-I derived proteins were chromatographically purified and analyzed, particularly by means of mass spectrometry and by way of determining the amino acid sequence from the N-terminus (Edman degradation). By these means truncations, particularly N-terminal truncations of hST6Gal-I were characterized in detail.

Several remarkable truncation variants were identified in the supernatants of transformed *Pichia* strains. The variants could possibly result from site-specific proteolytic cleavage during the course of secretion from the yeast cells, or result from endoproteolytic cleavage by one or more extracellular protease(s) present in the supernatant of cultured *Pichia* strains.

Each identified truncation variant was given a "delta" (="Δ") designation indicating the number of the last amino acid position of the respective truncation deletion, counted from the N-Terminus of the wild-type hST6Gal-I polypeptide according to SEQ ID NO:1 The particular N-terminal truncation variants Δ89 and Δ108 of hST6Gal-I were recombinantly expressed and studied in more detail.

Expression vectors were constructed for expression of hST6Gal-I wild-type protein as well as of the Δ89 and Δ108 truncation variants in various host organisms including prokaryotes such as *E. coli* and *Bacillus* sp., yeasts such as *Saccharomyces cerevisiae* and *Pichia pastoris*, and mammalian cells such as CHO cells and HEK cells. Vectors with expression constructs for the Δ89 and Δ108 truncation variants of hST6Gal-I were assembled molecularly thereby providing the means of recombinantly producing the Δ89 variant of human ST6Gal-I in several transformed host organisms. To facilitate purification of recombinantly expressed enzymes, the encoded truncation polypeptides encoded by the constructs optionally included a N-terminal His-tag, in specific embodiments.

An aspect and a specific embodiment of all other aspects as disclosed herein is a variant mammalian glycosyltransferase capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein. Particularly, the variant mammalian glycosyltransferase is capable of catalyzing formation of the α2,6 glycosidic bond of a N-acetylneuraminyl-α2,6-β-D-galactosyl-1,4-N-acetyl-β-D-glucosamine moiety in a glycoprotein glycan, thereby generating free N-acetylneuraminic acid. In a specific embodiment of all aspects as disclosed herein, the variant mammalian glycosyltransferase is a soluble enzyme comprising the amino acid motif from position 90 to position 108 in SEQ ID NO:1 disclosing human β-galactoside-α-2,6-sialyltransferase I. Encompassed by the teachings as disclosed in here are homologous sialyltransferases comprising an amino acid motif corresponding to the motif from position 90 to position 108 in SEQ ID NO:1.

In a specific embodiment of all aspects as disclosed herein, the variant mammalian glycosyltransferase capable of catalyzing hydrolysis of the α2,6 glycosidic bond is a mammalian glycosyltransferase is derived, by way of amino acid deletion, from human β-galactoside-α-2,6-sialyltransferase I according to SEQ ID NO:1, said sequence being truncated by a deletion from the N-terminus. In a further specific embodiment of all aspects as disclosed herein, the truncation deletion from the N-terminus is the contiguous sequence of position 1 to position 89 of SEQ ID NO:1.

Another aspect and a specific embodiment of all other aspects as disclosed herein is a fusion polypeptide comprising a polypeptide of a variant mammalian glycosyltransferase according to any embodiment as disclosed herein. A fusion protein or fusion polypeptide is a chimeric polypeptide comprising amino acid sequences of two or more polypeptides. The two or more polypeptides may have complementary functions, one of the polypeptides may provide a supplementary functional property, or one of the polypeptides may have a function unrelated to the others in the fusion polypeptide. One or more polypeptides comprising organelle targeting or retention sequences may be fused with a desired polypeptide to target the desired polypeptide to a specific cellular organelle, or retain the desired polypeptide within the cell. One or more polypeptides comprising a carrier sequence that aids in expression, purification and/or detection of the fusion polypeptide may be fused with a desired polypeptide (e.g., FLAG, a myc tag, a 6× His tag, GST fusions and the like). Particular fusion partners include N-terminal leader peptides capable of directing the variant mammalian glycosyltransferase portion of the fusion polypeptide to the secretory pathway of the host organism in which the fusion polypeptide is expressed. Thereby secretion in the extracellular space and the surrounding medium is facilitated. Yet, another aspect and a specific embodiment of all other aspects as disclosed herein is a nucleotide sequence encoding a variant mammalian glycosyltransferase according to any embodiment as disclosed herein or a fusion polypeptide comprising as a portion a variant mammalian glycosyltransferase according to any embodiment as disclosed herein. Importantly, the nucleotide sequence includes the sequence from position 90 to position 108 in SEQ ID NO:1, or the homologous equivalent thereof in the case of a sialyltransferase homologous to human β-galactoside-α-2,6-sialyltransferase I.

Yet, another aspect and a specific embodiment of all other aspects as disclosed herein is an expression vector comprising a target gene and sequences facilitating expression of the target gene in a host organism transformed with the expression vector, wherein the target gene comprises a nucleotide sequence as disclosed herein.

Yet, another aspect and a specific embodiment of all other aspects as disclosed herein is a transformed host organism, wherein the host organism is transformed with an expression vector as disclosed herein. With particular advantage, Human Embryonic Kidney 293 (HEK) cells can be used to practice the teachings as disclosed in here. A particular advantage of these cells is that they are very suited targets for transfection followed by subsequent culture and transient expression of the target gene. Thus, HEK cells can be efficiently used to produce target proteins by way of recombinant expression. With great advantage, expression constructs are designed to direct the translation products to the secretory pathway leading to secretion of the variant mammalian glycosyltransferase or a fusion polypeptide as disclosed herein. Nevertheless, Jurkat, NIH3T3, HeLa, COS and Chinese Hamster Ovary (CHO) cells are well-known alternatives and are included herein as alternative host organisms for transformation and specific embodiments of all aspects as disclosed herein.

Yet, another aspect and a specific embodiment of all other aspects as disclosed herein is a method to produce recombinantly a variant mammalian glycosyltransferase, the method comprising the step of expressing in a host organism transformed with an expression vector a nucleotide sequence encoding a variant mammalian glycosyltransferase as disclosed herein, wherein a polypeptide is formed, thereby producing variant mammalian glycosyltransferase.

According to earlier knowledge, N-terminally truncated variants of glycosyltransferases are advantageously used in vitro due to their lack of transmembrane domains. Thus, such variants are useful for catalyzing and performing glycosyltransferase reactions in solution. It was surprisingly found and is disclosed herein that particularly the N-terminally truncated variant Δ89 hST6Gal-I displays different activities in vitro, e.g. when incubated with glycosylated antibodies and in the presence of 5'-CMP. Thus, a specific embodiment of the present disclosure and all aspects and embodiments herein is a variant mammalian glycosyltransferase capable of catalyzing hydrolysis of a α2,6 glycosidic bond of a N-acetylneuraminyl-α2,6-β-D-galactosyl-1,4-N-acetyl-β-D-glucosamine moiety of a bi-sialylated glycoprotein, i.e. a glycoprotein comprising two separate terminal N-acetylneuraminyl-α2,6-β-D-galactosyl-1,4-N-acetyl-β-D-glucosamine moieties in one or more glycan portion(s) of the glycoprotein. In a specific embodiment, only one α2,6 glycosidic bond in a is hydrolyzed. In a further specific embodiment, the bi-sialylated glycoprotein is a bi-sialylated IgG immunoglobulin.

As an exemplary case, the IgG-Fc glycan G2 has two galactose moieties at the termini of the antennate branches which can be sialylated. Under suitable reaction conditions, the N-terminally truncated variant Δ89 hST6Gal-I catalyzes the synthesis of IgG with bi-sialylated G2 glycans (G2+2SA) at the immunoglobulin Fc portion. However, upon accumulation of 5'-CMP the enzyme variant acts as a sialidase catalyzing removal by hydrolysis of a sialic acid moiety from the bi-sialylated (G2+2SA) antibodies resulting in mono-sialylated (G2+1SA) antibodies. This property was found unexpectedly and appears to represent an intrinsic sialidase (neuraminidase) activity.

In a basic publication on human ST6Gal-I it was stated that the enzyme does not contain any sialidase activity, see Sticher et al. Glycoconjugate Journal 8 (1991) 45-54. In view of the present surprising finding it becomes possible to preferentially synthesize glycoproteins with mono-, bi- or even higher sialylated glycans, using the same enzyme and controlling the reaction kinetics of the enzyme by controlling CMP in the sialylation reaction mixture. A further advantage is that both activities, sialylation activity and sialidase activity are provided by the same enzyme, in the same reaction vessel.

The general finding documented in the present disclosure is, however, that there exists a variant mammalian glycosyltransferase, specifically a glycosyltransferase according to the present disclosure, which is capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein. In addition to the already known sialyltransferase (sialylation) activity the surprising finding was that at least as specifically shown for the N-terminally truncated human β-galactoside-α-2,6-sialyltransferase I having the amino acid sequence of SEQ ID NO:2 there is not only conventional sialyltransferase but also sialidase enzymatic activity mediated by this enzyme. Interestingly, in the exemplary cases these two activities were not observed at the same time, which may partly explain the unexpected finding. Thus, in the absence of CMP sialyltransferase activity dominates in the beginning and sialidase activity becomes apparent only at a later stage during the incubation, once sufficient amounts of CMP have accumulated. Nevertheless, the apparent recognition of two distinct activities of the same enzyme allows to control the extent of sialylation of target molecules, e.g. by way of varying incubation time.

However, in a very elegant way, sialylation can be maximized by adding to the sialylation reaction mixture an enzyme capable of hydrolyzing the phosphoester bond in 5'-cytidine-monophosphate under the conditions which permit sialyltransferase enzymatic activity. Thus, the by-product CMP is removed and the sialylation catalysis by the sialyltransferase is not counteracted.

Yet, another aspect and a specific embodiment of all other aspects as disclosed herein is the use of an enzyme capable of hydrolyzing the phosphoester bond in 5'-cytidine-monophosphate under the conditions which permit sialyltransferase enzymatic activity to maintain glycosyltransferase activity and/or inhibit sialidase activity of a variant mammalian glycosyltransferase as disclosed herein, specifically the N-terminally truncated human β-galactoside-α-2,6-sialyltransferase I having the amino acid sequence of SEQ ID NO:2.

Such controlled sialylation is provided as a novel means to synthesize in vitro mono-, bi-, and higher sialylated glycoproteins with a desired degree of sialylation. Thus, though exemplified by showing the desired technical effects with IgG molecules, the uses according to the disclosures in here also allow to process other glycoproteins in a similar way, with the proviso that concerning glycosyltransferase activity, the glycoproteins comprise two or more terminal antennate β-D-galactosyl-1,4-N-acetyl-β-D-glucosamine moieties. The same reasoning applies in an analogous way to glycolipids.

In a particular example, recombinant humanized IgG1 and IgG4 monoclonal antibodies (mabs), characterized as G2+0SA (=two acceptor sites present, no sialylation at any acceptor site), as well as EPO (=erythropoietin) were used as targets in sialylation experiments (30 µg enzyme/300 µg target protein). Δ89 hST6Gal-I was used under standard reaction conditions and the G2+0SA, G2+1SA (=monosialylation, one out of two acceptor sites is sialylated) and G2+2SA (=bi-sialylation, both possible acceptor sites are sialylated) status was analyzed by mass spectrometry.

Due to the high expression rates and the efficient purification procedures the exemplary Δ89 hST6Gal-I but also functionally equivalent enzymes can be made available in large quantities and with high purity. The variant Δ89 hST6Gal-I enzyme is active with high molecular weight substrates of which monoclonal antibodies are just one example. Depending on the incubation time, Δ89 hST6Gal-I in combination with a CMP-hydrolyzing enzyme shows good performance in sialylation experiments using monoclonal antibodies with bi-antennary glycan as substrate. Using embodiments of the present disclosure the preferably bi-sialylated glycans are obtained with great advantage after shorter incubation periods, such as 8 hours. Tetra-antennary glycans are also accepted as substrate (data not shown). The results demonstrate technical advantage for in vitro glycoengineering of therapeutic antibodies.

The following items further provide specific aspects of the disclosure, and specific embodiments to practice the teachings provided herein.

1. Use of a soluble human β-galactoside-α-2,6-sialyltransferase I comprising the amino acid motif from position 90 to position 108 in SEQ ID NO:1 for in vitro hydrolyzing in the presence of 5'-cytidine-monophosphate the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid.
2. The use according to item 1, wherein the soluble human β-galactoside-α-2,6-sialyltransferase I comprises the amino acids from position 90 to position 406 in SEQ ID NO:1.
3. The use according to any of the items 1 and 2, wherein the amino acid sequence of the soluble β-galactoside-α-2,6-sialyltransferase I is the amino acid sequence of SEQ ID NO:2.
4. The use according to any of the items 1 to 3, wherein the glycoprotein is selected from the group consisting of a cell surface glycoprotein and a serum glycoprotein.
5. The use according to item 4, wherein the serum glycoprotein is selected from a glycosylated protein signaling molecule, a glycosylated immunoglobulin, and a glycosylated protein of viral origin.
6. The use according to any of the items 1 to 5, wherein the glycoprotein is recombinantly produced.
7. The use according to item 6, wherein the glycoprotein is recombinantly produced in a transformed host cell of mammalian origin.
8. The use according to any of the items 1 to 7, wherein the glycoprotein is an immunoglobulin of human origin or a humanized immunoglobulin, the immunoglobulin being selected from the group consisting of IgG1, IgG2, IgG3, IgG4.
9. The use according to any of the items 1 to 7, wherein the glycoprotein is selected from EPO and asialofetuin.
10. An aqueous composition comprising
    (a) a soluble human β-galactoside-α-2,6-sialyltransferase I comprising the amino acid motif from position 90 to position 108 in SEQ ID NO:1;
    (b) cytidine-5'-monophospho-N-acetylneuraminic acid, or a functional equivalent thereof;
    (c) a glycosylated target molecule selected from a glycoprotein and a glycolipid, the target molecule comprising one or more antenna(e), at least one antenna having as a terminal structure a β-D-galactosyl-1,4-N-acetyl-β-D-glucosamine moiety with a hydroxyl group at the C6 position in the galactosyl residue;
    (d) an aqueous solution permitting glycosyltransferase enzymatic activity;
    wherein the aqueous composition further comprises an enzyme capable of hydrolyzing the phosphoester bond in 5'-cytidine-monophosphate under conditions permitting glycosyltransferase enzymatic activity.
11. The aqueous composition according to item 10, wherein the soluble human β-galactoside-α-2,6-sialyltransferase I comprises the amino acids from position 90 to position 406 in SEQ ID NO:1.
12. The aqueous composition according to any of the items 10 and 11, wherein the amino acid sequence of the soluble β-galactoside-α-2,6-sialyltransferase I is the amino acid sequence of SEQ ID NO:2.
13. The aqueous composition according to any of the items 10 to 12, wherein the glycosylated target molecule is a glycoprotein selected from the group consisting of a cell surface glycoprotein and a serum glycoprotein.
14. The aqueous composition according to any of the items 10 to 13, wherein the serum glycoprotein is selected from a glycosylated protein signaling molecule, a glycosylated immunoglobulin, and a glycosylated protein of viral origin.
15. The aqueous composition according to any of the items 10 to 14, wherein the glycoprotein is recombinantly produced.
16. The aqueous composition according to item 15, wherein the glycoprotein is recombinantly produced in a transformed host cell of mammalian origin.
17. The aqueous composition according to any of the items 10 to 16, wherein the glycoprotein is an immunoglobulin of human origin or a humanized immunoglobulin, the immunoglobulin being selected from the group consisting of IgG1, IgG2, IgG3, IgG4.
18. The aqueous composition according to any of the items 10 to 16, wherein the glycoprotein is selected from EPO and asialofetuin.
19. The aqueous composition according to any of the items 10 to 18, wherein the aqueous solution comprises water, a buffer salt capable of buffering in the pH range of pH 6 to pH 8, and optionally a compound selected from the group consisting of a neutral salt, a salt with a divalent cation, an antioxidant, a surfactant and a mixture thereof.
20. The aqueous composition according to any of the items 10 to 19, the composition having a temperature of 0° C. to 40° C.
21. The aqueous composition according to any of the items 10 to 20, wherein the enzyme capable of the hydrolyzing phosphoester bond in 5'-cytidine-monophosphate is selected from the group consisting of an alkaline phosphatase, an acid phosphatase, and a 5' nucleotidase.
22. The aqueous composition according to item 21, wherein the alkaline phosphatase is selected from the group consisting of alkaline phosphatase of bacterial origin, shrimp alkaline phosphatase, calf intestine alkaline phosphatase, human placental alkaline phosphatase, and a mixture thereof.
23. The aqueous composition according to item 22, wherein the aqueous composition further comprises $Zn^{2+}$ ions.
24. The aqueous composition according to item 21, wherein the 5' nucleotidase is 5' nucleotidase CD73 of mammalian origin, specifically of human origin.
25. Use of an aqueous composition according to any of the items 10 to 24 for reducing 5'-cytidine-monophosphate-mediated inhibition and thereby maintaining the sialylating activity of the soluble human β-galactoside-α-2,6-sialyltransferase I comprising the amino acid motif from position 90 to position 108 in SEQ ID NO: 1.
26. The use according to item 25, wherein the sialylating activity catalyzes transfer and covalent coupling of the sialic acid residue, or the functional equivalent thereof, from the co-substrate to a β-D-galactosyl-1,4-N-acetyl-β-D-glucosamine moiety with a hydroxyl group at the C6 position in the galactosyl residue, the moiety being a terminal structure of a glycan of a glycosylated target molecule selected from a glycoprotein and a glycolipid.
27. A method of producing in vitro a sialylated target molecule, the method comprising the steps of
    (a) providing an aqueous composition according to any of the items 10 to 24;

(b) forming one or more terminal antennal N-acetyl-neuraminyl-α2,6-β-D-galactosyl-1,4-N-acetyl-β-D-glucosamine residue(s) by incubating the aqueous composition of step (a), thereby reacting cytidine-5'-monophospho-N-acetylneuraminic acid, or a functional equivalent thereof, as co-substrate, thereby forming 5'-cytidine-monophosphate;

(c) hydrolyzing the phosphoester bond of the 5'-cytidine-monophosphate formed in step (b), thereby reducing 5'-cytidine-monophosphate-mediated inhibition, thereby maintaining the activity of the soluble human β-galactoside-α-2,6-sialyltransferase I;

thereby producing in vitro the sialylated target molecule.

28. The method according to item 27, wherein the method is performed at a temperature of 0° C. to 40° C.

29. The method according to any of the items 27 and 28, wherein steps (b) and (c) are performed in the same vessel.

30. The method according to any of the items 27 to 29, wherein steps (b) and (c) are performed for a period selected from the group consisting of 2 h to 96 h, 2 h to 23 h, 2 h to 6 h, and about 2 h.

31. The method according to any of the items 27 to 29, wherein steps (b) and (c) are performed for a period selected from the group consisting of 6 h to 96 h, 6 h to 23 h, and about 6 h.

32. The method according to any of the items 27 to 29, wherein steps (b) and (c) are performed for a period selected from the group consisting of 23 h to 96 h, and about 23 h.

33. The method according to any of the items 27 to 29, wherein steps (b) and (c) are performed for a period of about 96 h.

34. Use of a soluble human β-galactoside-α-2,6-sialyltransferase I lacking the amino acid motif from position 90 to position 108 in SEQ ID NO:1 for transferring in vitro and in the presence of 5'-cytidine-monophosphate a 5-N-acetylneuraminic acid residue from the donor compound cytidine-5'-monophospho-N-acetylneuraminic acid, or from a functional equivalent thereof, to an acceptor, the acceptor being terminal β-D-galactosyl-1,4-N-acetyl-3-D-glucosamine in a glycan moiety of a glycoprotein or a glycolipid.

35. The use according to item 34, wherein the soluble human β-galactoside-α-2,6-sialyltransferase I comprises the amino acids from position 109 to position 406 in SEQ ID NO:1.

36. The use according to any of the items 34 and 35, wherein the amino acid sequence of the soluble β-galactoside-α-2,6-sialyltransferase I is the amino acid sequence of SEQ ID NO:5.

37. The use according to any of the items 34 to 36, wherein the glycoprotein is selected from the group consisting of a cell surface glycoprotein and a serum glycoprotein.

38. The use according to item 37, wherein the serum glycoprotein is selected from a glycosylated protein signaling molecule, a glycosylated immunoglobulin, and a glycosylated protein of viral origin.

39. The use according to any of the items 34 to 38, wherein the glycoprotein is recombinantly produced.

40. The use according to item 39, wherein the glycoprotein is recombinantly produced in a transformed host cell of mammalian origin.

41. The use according to any of the items 34 to 40, wherein the glycoprotein is an immunoglobulin of human origin or a humanized immunoglobulin, the immunoglobulin being selected from the group consisting of IgG1, IgG2, IgG3, IgG4.

42. The use according to any of the items 34 to 40, wherein the glycoprotein is selected from EPO and asialofetuin.

43. An aqueous composition comprising
(a) a soluble human β-galactoside-α-2,6-sialyltransferase I lacking the amino acid motif from position 90 to position 108 in SEQ ID NO:1;
(b) cytidine-5'-monophospho-N-acetylneuraminic acid, or a functional equivalent thereof;
(c) a glycosylated target molecule selected from a glycoprotein and a glycolipid, the target molecule comprising one or more antenna(e), at least one antenna having as a terminal structure a β-D-galactosyl-1,4-N-acetyl-β-D-glucosamine moiety with a hydroxyl group at the C6 position in the galactosyl residue;
(d) an aqueous solution permitting glycosyltransferase enzymatic activity;
wherein the aqueous composition further comprises 5'-cytidine-monophosphate.

44. The aqueous composition according to item 43, wherein the soluble human β-galactoside-α-2,6-sialyltransferase I comprises the amino acids from position 109 to position 406 in SEQ ID NO:1.

45. The aqueous composition according to any of the items 43 and 44, wherein the amino acid sequence of the soluble β-galactoside-α-2,6-sialyltransferase I is the amino acid sequence of SEQ ID NO:5.

46. The aqueous composition according to any of the items 43 to 45, wherein the glycosylated target molecule is a glycoprotein selected from the group consisting of a cell surface glycoprotein and a serum glycoprotein.

47. The aqueous composition according to any of the items 43 to 46, wherein the serum glycoprotein is selected from a glycosylated protein signaling molecule, a glycosylated immunoglobulin, and a glycosylated protein of viral origin.

48. The aqueous composition according to any of the items 43 to 47, wherein the glycoprotein is recombinantly produced.

49. The aqueous composition according to item 48, wherein the glycoprotein is recombinantly produced in a transformed host cell of mammalian origin.

50. The aqueous composition according to any of the items 43 to 49, wherein the glycoprotein is an immunoglobulin of human origin or a humanized immunoglobulin, the immunoglobulin being selected from the group consisting of IgG1, IgG2, IgG3, IgG4.

51. The aqueous composition according to any of the items 43 to 49, wherein the glycoprotein is selected from EPO and asialofetuin.

52. The aqueous composition according to any of the items 43 to 51, wherein the aqueous solution comprises water, a buffer salt capable of buffering in the pH range of pH 6 to pH 8, and optionally a compound selected from the group consisting of a neutral salt, a salt with a divalent cation, an antioxidant, a surfactant and a mixture thereof.

53. The aqueous composition according to any of the items 43 to 52, the composition having a temperature of 0° C. to 40° C.

54. A method of producing in vitro a sialylated target molecule, the method comprising the steps of
(a) providing an aqueous composition according to any of the items 43 to 53;
(b) forming one or more terminal antennal N-acetyl-neuraminyl-α2,6-β-D-galactosyl-1,4-N-acetyl-β-D- glucosamine residue(s) by incubating the aqueous composition of step (a), thereby reacting cytidine-5'-monophospho-N-acetylneuraminic acid, or a functional equivalent thereof, as co-substrate, thereby forming 5'-cytidine-monophosphate;

(c) accumulating 5'-cytidine-monophosphate formed in step (b);

thereby producing in vitro the sialylated target molecule.

55. The method according to item 54, wherein the method is performed at a temperature of 0° C. to 40° C.
56. The method according to any of the items 54 and 55, wherein steps (b) and (c) are performed in the same vessel.
57. The method according to any of the items 54 to 56, wherein steps (b) and (c) are performed for a period selected from the group consisting of 2 h to 72 h.
58. Use of an enzyme capable of the hydrolyzing phosphoester bond in 5'-cytidine-monophosphate for maintaining sialyltransferase enzymatic activity in a composition according to any of the items 10 to 24.
59. Use of an enzyme capable of the hydrolyzing phosphoester bond in 5'-cytidine-monophosphate for inhibiting sialidase enzymatic activity in a composition according to any of the items 10 to 24.
60. A preparation of sialylated immunoglobulins, each immunoglobulin having a plurality of acceptor sites for human β-galactoside-α-2,6-sialyltransferase I, wherein less than 25% of the acceptor sites in the preparation of sialylated immunoglobulins are not sialylated, and 75% or more are sialylated, wherein the preparation is obtained by a method according to any of the items 27 to 33.
61. The preparation according to item 60, wherein less than 20% of the acceptor sites in the preparation of sialylated immunoglobulins are not sialylated, and 80% or more are sialylated.
62. The preparation according to item 60, wherein less than 10% of the acceptor sites in the preparation of sialylated immunoglobulins are not sialylated, and 90% or more are sialylated.

The Examples that follow are illustrative of specific embodiments of the disclosure, and various uses thereof. They set forth for explanatory purposes only, and are not to be taken as limiting the disclosure.

Example 1

Test for Sialyltransferase Enzymatic Activity

Asialofetuin (desialylated fetuin, Roche Applied Science) was used as acceptor and CMP-9-fluoro-NANA (CMP-9-fluoresceinyl-NeuAc) was used as donor substrate (Brossmer, R. & Gross H. J. (1994) Meth. Enzymol. 247, 177-193). Enzymatic activity of a sialyltransferase was determined by measuring the transfer of sialic acid from the donor compound to asialofetuin. The reaction mix (35 mM MES, pH 6.0, 0.035% TRITON™ X-100 (Octylphenol Ethoxylate), 0.07% BSA) contained 2.5 µg of enzyme sample, 5 µL asialofetuin (20 mg/mL) and 2 µL CMP-9-fluoro-NANA (1.0 mg/mL) in a total volume of 51 µL. The reaction mix was incubated at 37° C. for 30 min. The reaction was stopped by the addition of 10 µL of the inhibitor CTP (10 mM). The reaction mix was loaded onto a PD10 desalting column equilibrated with 0.1 M Tris/HCl, pH 8.5. Fetuin was eluted from the column using the equilibration buffer. The fractions size was 1 mL. The concentration of formed fetuin was determined using a fluorescence spectrophotometer. Excitation wave length was 490 nm, emission was measured at 520 nm. Enzymatic activity was expressed as RFU (relative fluorescence unit). 10,000 RFU/µg is equivalent to a specific activity of 0.0839 nmol/µg× min.

Example 2

SDS Gel Electrophoresis

Analytical SDS gel electrophoresis was carried out using NuPAGE gels (4-12%, Invitrogen). Samples (36 µL) were diluted with 12 µL NuPAGE LDS sample buffer (Invitrogen) and incubated for 2 min at 85° C. Aliquots, typically containing 5 µg protein were loaded on the gel. The gels were stained using SimplyBlue SafeStain (Invitrogen).

Example 3

N-Terminal Sequencing by Edman Degradation

The N-terminal sequences of expressed variants of human ST6Gal-I were analyzed by Edman degradation using reagents and devices obtained from Life Technologies. Preparation of the samples was done as described in the instruction manual of the Life Technologies ProSorb Sample Preparation cartridges (catalogue number 401950) and the Life Technologies ProBlott Mini PK/10 membranes (catalogue number 01194). For sequencing the Procise Protein Sequencing Platform was used.

Example 4

Mass Spectrometry of Glycosylated Human ST6Gal-I Enzymes

The molecular masses of variants of human ST6Gal-I expressed in HEK cells were analyzed. Glycosylated forms of human ST6Gal-I were prepared, and prepared material was analyzed using Micromass Q-Tof Ultima and Synapt G2 HDMS devices (Waters UK) and MassLynx V 4.1 software.

For mass spectrometry measurement the samples were buffered in electrospray medium (20% acetonitrile+1% formic acid). The buffer exchange was performed with Illustra™ MicroSpin™ G-25 columns (GE-Healthcare). 20 µg sialyltransferase variant with a concentration of 1 mg/mL was applied to the pre-equilibrated column and evaluated by centrifugation. The resulting eluate was analyzed by electrospray ionization mass spectrometry.

Example 5

Mass Spectrometry of Deglycosylated Human ST6Gal-I Enzymes

The molecular masses of variants of human ST6Gal-I expressed in HEK cells were analyzed. Delycosylated forms of human ST6Gal-I were analyzed using Micromass Q-Tof Ultima and Synapt G2 HDMS devices (Waters UK) and MassLynx V 4.1 software.

For deglycosylation samples of the sialyltransferase were denatured and reduced. To 100 µg sialyltransferase 45 µL denaturing buffer (6 M guanidinium hydrochloride) and 13 µL TCEP (=tris(2-carboxyethyl)phosphine; 0.1 mM, diluted in denaturing buffer) were added. Further the appropriate volume of ultrapure water was added, so that the overall concentration of guanidinium hydrochloride was about 4 M. After incubation of the sample for 1 h at 37° C. the buffer was changed using a Bio-Spin® 6 Tris column (Bio Rad), which was pre-equilibrated with ultrapure water. The whole sample was applied onto the column and eluted by centrifugation. To the resulting eluate 5.5 µL of 0.1 U/µL solution of PNGase-F was added and incubated at 37° C. over night. Afterwards the samples were adjusted to 30% ACN (=acetonitrile) and 1% FA (=formamide) and analyzed by electrospray ionization mass spectrometry.

Example 6

Cloning of pM1MT Expression Constructs for Transient Expression in Mammalian Host Cells of Truncated Variant Δ89 of Human ST6Gal-I Truncated variant Δ89 of human ST6Gal-I was cloned for transient expression using an Erythropoietin signal peptide sequence (Epo) and a peptide spacer of two amino acids ("AP"). For the Epo-AP-Δ89 hST6Gal-I construct codon-optimized cDNAs were synthesized, see SEQ ID NO:3. Instead of the natural leader sequences and the N-terminal protein sequences, the hST6Gal-I coding region harbors the Erythropoietin signal sequence plus AP linker sequence in order to ensure correct processing of expressed polypeptides by the secretion machinery of the host cell line. In addition, the expression cassettes features SalI and BamHI restriction sites for cloning into the multiple cloning site of the predigested pM1MT vector fragment (Roche Applied Science). Expression of the ST6Gal-I coding sequence is therefore under control of a human cytomegalovirus (CMV) immediate-early enhancer/promoter region, followed by an "intron A" for regulated expression, and a BGH polyadenylation signal.

Expression of the Epo-AP-Δ89 hST6Gal-I construct in HEK cells, and secretion of Δ89 hST6Gal-I protein into cell supernatant was performed as described in Example 8.

Example 7

Cloning of pM1MT Expression Constructs for Transient Expression in Mammalian Host Cells of Truncated Variant Δ108 of human ST6Gal-I Truncated variant Δ108 of human ST6Gal-I was cloned for transient expression using an Erythropoietin signal peptide sequence (Epo) and a peptide spacer of four amino acids ("APPR"). For the Epo-APPR-Δ108 hST6Gal-I construct a codon-optimized cDNAs was synthesized, see SEQ ID NO:6. The natural hST6Gal-I-derived mRNA leader and N-terminal protein sequences were exchanged with the Erythropoietin signal sequence and the "APPR" linker sequence to ensure correct processing of the polypeptide by the secretion machinery of the HEK host cell line. In addition, the expression cassettes feature SalI and BamHI sites for cloning into the multiple cloning site of the pre-digested pM1MT vector fragment (Roche Applied Science). Expression of the hST6Gal-I coding sequence was thereby put under the control of a human cytomegalovirus (CMV) immediate-early enhancer/promoter region; the expression vector further featured an "intron A" for regulated expression and a BGH polyadenylation signal.

Expression of the Epo-APPR-Δ108 hST6Gal-I construct (SEQ ID NO:6) in HEK cells, and secretion of Δ108 hST6Gal-I protein into cell supernatant was performed as described in Example 8.

Example 8

Transformation HEK Cells and Transient Expression and Secretion

Transient gene expression (TGE) by transfection of plasmid DNA is a rapid strategy to produce proteins in mammalian cell culture. For high-level expression of recombinant human proteins a TGE platform based on a suspension-adapted human embryonic kidney (HEK) 293 cell line was used. Cells were cultured in shaker flasks at 37° C. under serum-free medium conditions. The cells were transfected at approx. 2×10$^6$ vc/mL with the pM1MT expression plasmids (0.5 to 1 mg/L cell culture) complexed by the 293-Free™ (Merck) transfection reagent according to the manufacturer's guidelines. Three hours post-transfection, valproic acid, a HDAC inhibitor, was added (final conc. 4 mM) in order to boost the expression (Backliwal et al. (2008), Nucleic Acids Research 36, e96). Each day, the culture was supplemented with 6% (v/v) of a soybean peptone hydrolysate-based feed. The culture supernatant was collected at day 7 post-transfection by centrifugation.

Example 9

Purification of the N-Terminal Truncation Variants of Human ST6Gal-I from Supernatants of Transformed HEK Cells HEK cells were transformed as described in Example 8. Expression constructs were prepared as described in Examples 6 and 7.

From supernatants of HEK cell fermentations the two enzyme variants Epo-AP-Δ89 hST6Gal-I and Epo-APPR-Δ108 hST6Gal-I were purified using a simplified purification protocol. In a first step, a volume of 0.1 L of culture supernatant was filtrated (0.2 μm), and the solution was dialysed against buffer A (20 mM potassium phosphate, pH 6.5). The dialysate was loaded onto a S-Sepharose™ ff (Fast Flow) column (1.6 cm×2 cm) equilibrated with buffer A. After washing with 100 mL buffer A, the enzyme was eluted with a linear gradient of 10 mL buffer A and 10 mL of buffer A with 200 mM NaCl, followed by a wash step using 48 mL of buffer A with 200 mM NaCl. Fractions (4 mL) were analysed by an analytical SDS gel electrophoresis.

Fractions containing the Δ89 hST6Gal-I enzyme were pooled and dialyzed against buffer B (50 mM MES, pH 6.0). The dialyzed pool was loaded onto a Heparin Sepharose ff column (0.5 cm×5 cm) equilibrated with buffer B and eluted using buffer B with 200 mM NaCl. Fractions (1 mL) containing the enzyme were pooled and dialyzed against buffer B. Protein concentrations were determined at 280 nm (E280 nm [1 mg/mL]=1.931). Mass spectrometry analysis showed that the recombinantly expressed Epo-AP-Δ89 hST6Gal-I enzyme was secreted without the N-terminal amino acids AP. This finding was unexpected and indicated unusual cleavage of the expressed protein by the signal peptidase while removing the Epo portion. For the recombinant human Δ89 hST6Gal-I enzyme a specific activity of 3.75 nmol/μg×min was determined. FIG. 2 shows the results of a SDS-PAGE of recombinant Δ89 hST6Gal-I variant purified from HEK cells.

Figure 3:
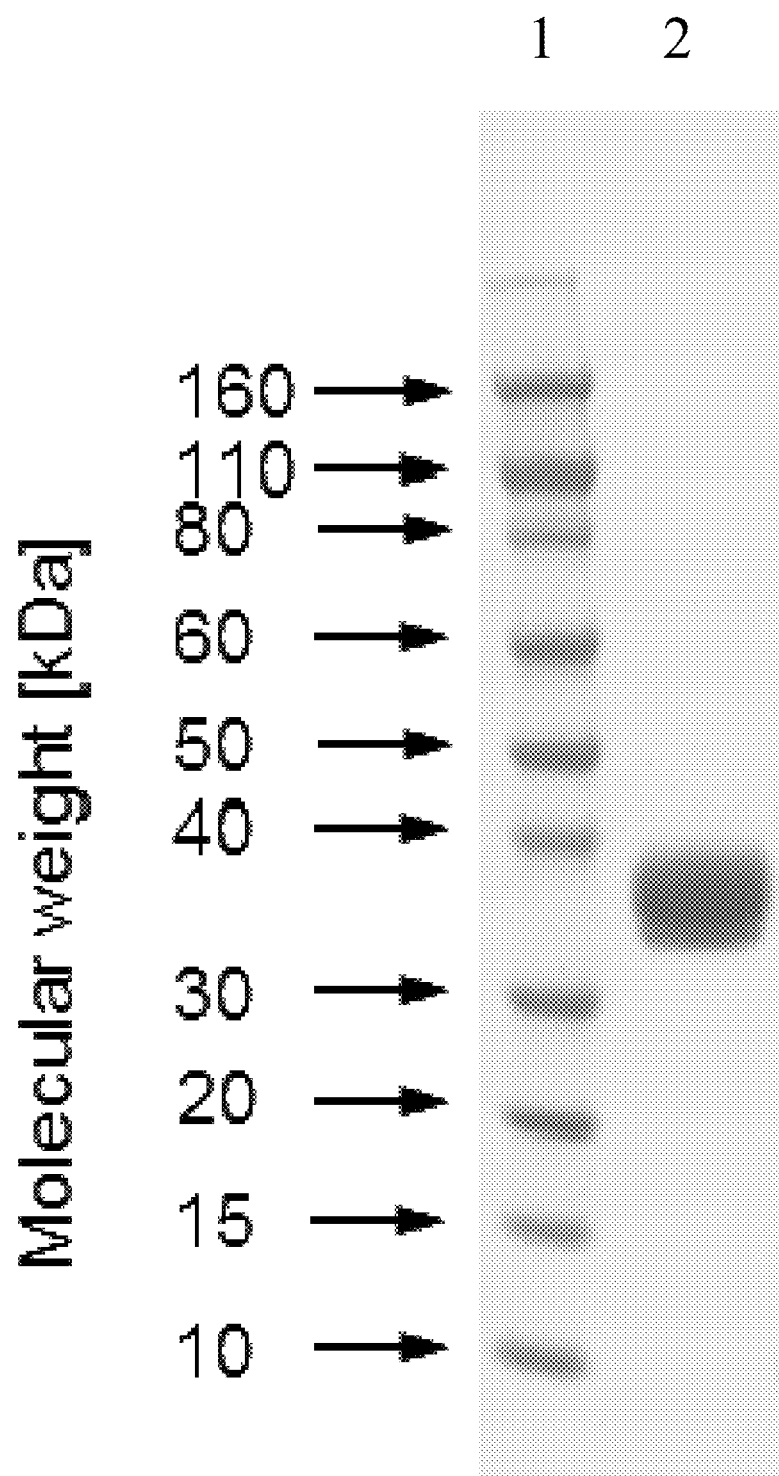
FIG. 3 SDS gel after electrophoresis and staining of the Δ108 hST6Gal-I variant transiently expressed in and secreted from HEK cells. Lane 1 shows a size-standard, molecular weights in kDa according to the standard are indicated to the left. Lane 2: Δ108 hST6Gal-I truncation variant (5 µg of protein were loaded on the gel).

Fractions containing the Δ108 hST6Gal-I enzyme were pooled and dialyzed against storage buffer (20 mM potassium phosphate, 100 mM sodium chloride, pH 6.5). Protein concentration was determined at a wave length of 280 nm using a molar extinction coefficient of 1.871. Mass spectrometric analysis of the recombinant protein secreted from the HEK cells transformed with the Epo-APPR-Δ108-hST6Gal-I expression construct confirmed the N-terminal sequence "APPR", thus indicating the expected cleavage of the EPO signal sequence by the signal peptidase. For the recombinant human Δ108 hST6Gal-I variant from HEK cells a specific activity of >600 RFU/μg was determined. FIG. 3 shows the results of a SDS-PAGE of recombinant Δ108 hST6Gal-I variant purified from HEK cells.

Example 10

Sialylation of Humanized Monoclonal Antibody IgG4 MAB Using Δ89 hST6Gal-I

Figure 4:
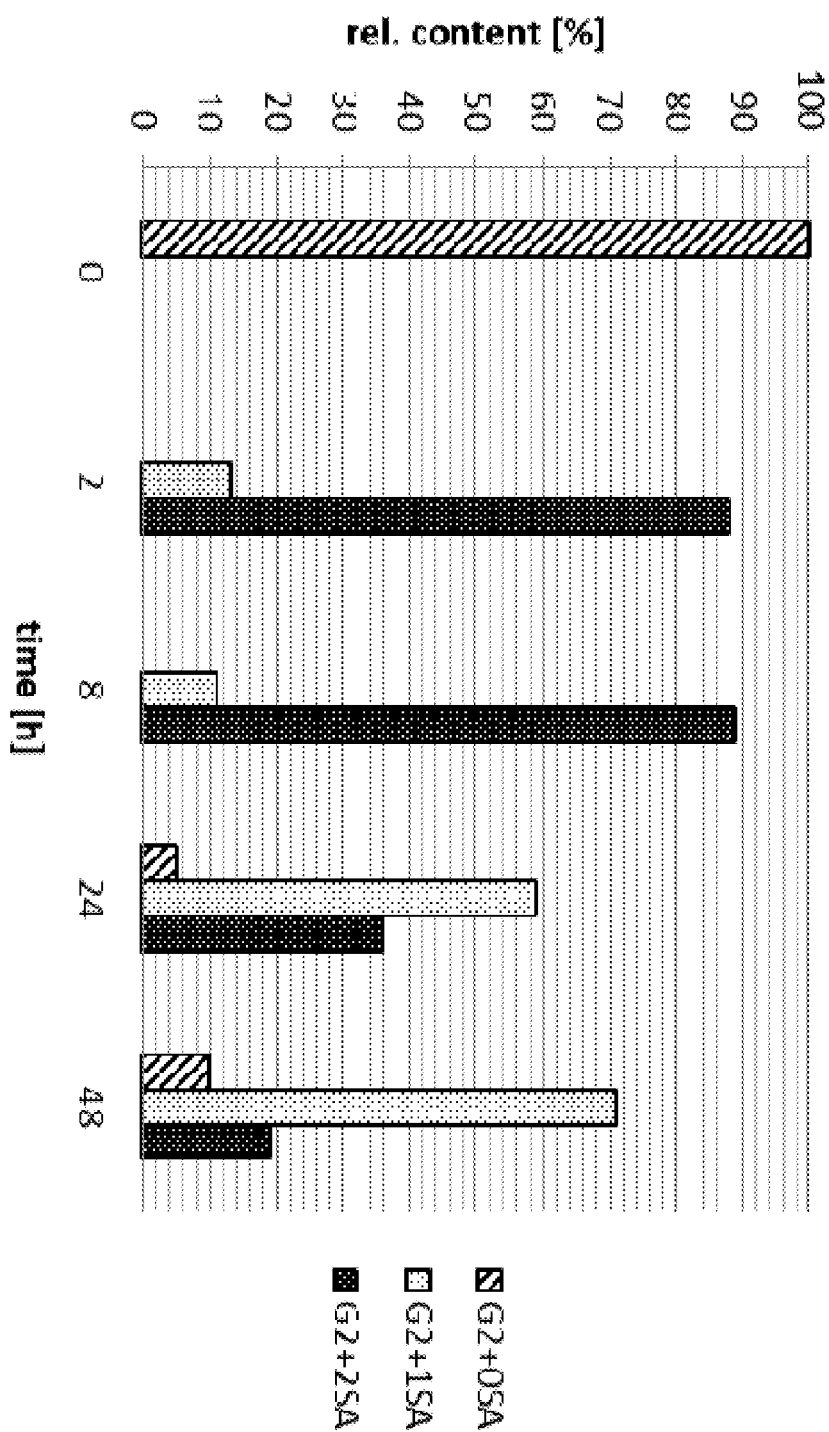
FIG. 4 Time course of sialylation of IgG4 MAB using recombinant Δ89 hST6Gal-I.

A highly galactosylated humanized monoclonal antibody IgG4 MAB was used in sialylation experiments. The reaction mixture contained IgG4 MAB (300 µg in 55 µL 35 mM sodium acetate/Tris buffer pH 7.0), the donor substrate CMP-NANA (150 µg in 50 µL water) and sialyltransferase (30 µg Δ89 hST6Gal-I in 20 mM potassium phosphate, 0.1 M NaCl, pH 6.5). The samples were incubated at 37° C. for a defined time. To stop the reaction the samples were frozen at −20° C. For mass analysis 100 µL denaturing buffer (6 M guanidinium chloride) and 30 µL TCEP (=tris(2-carboxyethyl)phosphine; 0.1 mM, diluted in denaturing buffer) were added to the samples and the samples were incubated at 37° C. for 1 h. The samples were buffered in electrospray medium [20% ACN (=acetonitrile), 1% FA (=formamide)] using pre-equilibrated Illustra™ Nap5-Columns (GE-Healthcare). Samples were analyzed by electrospray ionization mass spectrometry and the content of G2+0SA, G2+1SA and G2+2SA N-glycans was determined. A Micromass Q-Tof Ultima and a Synapt G2 HDMS device (Waters UK) were used, the software used was MassLynx V 4.1. To determine the kinetics of the sialylation the reaction was incubated up to 72 h. FIG. 4 shows the relative amounts of differently sialylated target proteins obtained after different time points during the incubation period.

The content of G2+0SA, G2+1SA and G2+2SA was determined by mass spectrometry. For the variant Δ89 hST6Gal-I already after 2 h of incubation a high content (88%) of the bi-sialylated form G2+2SA was obtained, see FIG. 4. The data also show that the content of G2+0SA and G2+1SA again increased over time due to the intrinsic CMP-dependent sialidase (neuraminidase) activity of Δ89 hST6Gal-I. After an incubation of 48 h a G2+1SA content of 71% was obtained.

Figure 5:
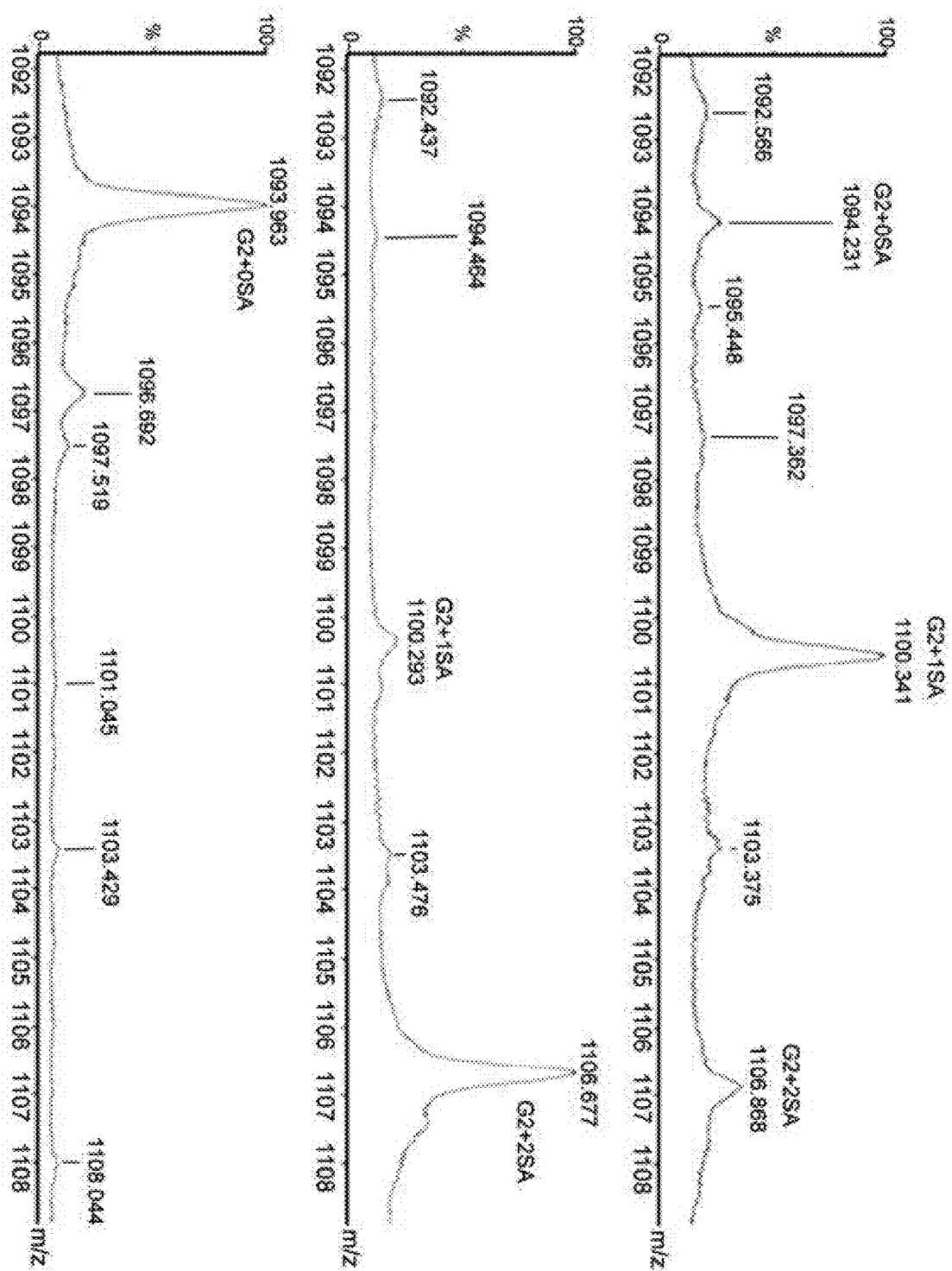
FIG. 5 Kinetics of formation of G2+2SA and G2+1SA, catalyzed by recombinant Δ89 hST6Gal-I, as shown by mass spectra taken as a basis for determination of the relative content of the different sialylated target molecule species.

FIG. 5 shows the spectra obtained by mass spectrometric analysis of different samples of IgG4 MAB. Samples were taken at time point t=0 (lower panel), time point t=8 h (middle panel) and time point t=48 h (upper panel). The mass over charge (m/z) signals of one charge state in the mass spectrum of the IgG molecule with G2+0SA, G2+1SA and G2+2SA glycans are depicted. The relative intensities of the different sialylated species are derived from these signals. Corresponding to FIG. 4, at t=0 h G2+0SA is the major glycan species. At t=8 h the signal for G2+2SA is the dominant form whereas at t=48 h, G2+1SA is the most abundant species. For the determined numerical values see FIG. 4.

Example 11

Inhibition of Sialidase Activity of Δ89 hST6Gal-I by CTP

Figure 6:
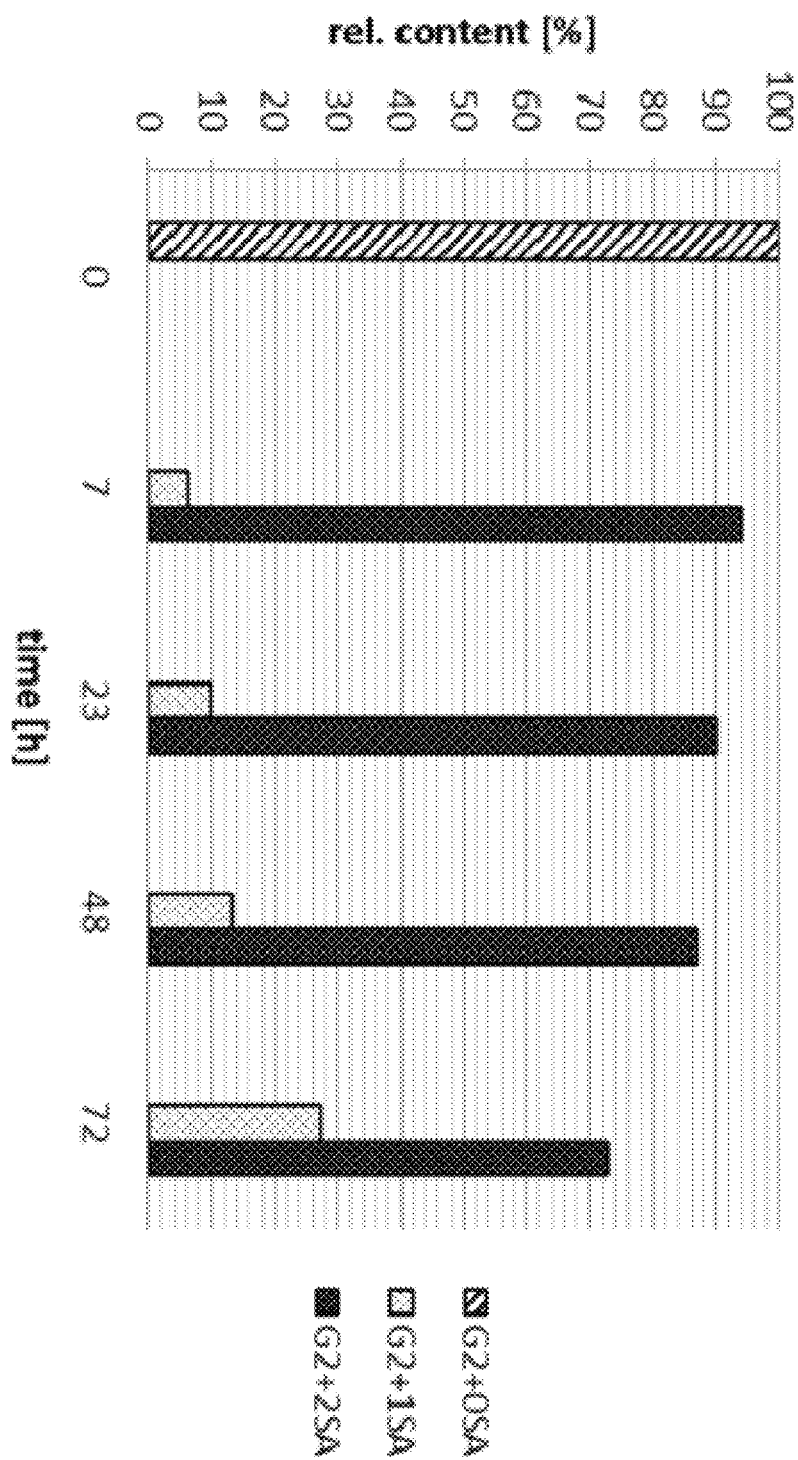
FIG. 6 Inhibition of sialidase activity of recombinant Δ89 hST6Gal-I by CTP. The relative content of antibodies with glycan with terminal galactose residues (G2+0SA, "asialo"), mono-sialylated glycan (G2+1SA) and bi-sialylated glycan (G2+2SA) is shown for different time points.

The compound cytidine-5′-triphosphate (CTP) is a known potent inhibitor of sialyltransferases (Scudder P R & Chantler E N BBA 660 (1981) 136-141). To demonstrate that the sialidase activity is an intrinsic activity of Δ89 hST6Gal-I, inhibition experiments were performed. In the first phase of the experiment the sialylation of IgG4 MAB by Δ89 hST6Gal-I was performed to achieve a high content of G2+2SA (see Example 10). After 7 h of incubation the G2+2SA content was 94%. Subsequently, CTP was added to inhibit the sialidase activity of Δ89 hST6Gal-I (final concentration of CTP: 0.67 mM). At different times samples were taken and the content of G2+0SA, G2+1SA and G2+2SA was determined by mass spectrometry. The results are shown in FIG. 6. Compared to inhibitor-free conditions shown in FIG. 4 the degradation of G2+2SA caused by the sialidase activity was significantly reduced. After 72 h of incubation 73% of G2+2SA were still present. The inhibition of the sialidase activity by a known inhibitor of sialyltransferase activity strongly indicates that both activities are located in the same active center of Δ89 hST6Gal-I.

Example 12

Sialylation of IgG1 MAB with Δ89 hST6Gal-I

The amount of 15 mg of a highly galactosylated humanized monoclonal antibody IgG1 MAB was used for sialylation treatment. The reaction mixture contained defined amounts of IgG1 MAB (15 mg in 1,854 µL aqueous buffer containing 20 mM sodium acetate, 50 mM Tris buffer, pH 8.0), the donor substrate CMP-NANA (7,500 µg in 2,500 µL water) and sialyltransferase (1,500 µg recombinantly produced and purified Δ89 hST6Gal-I in 202 µL of 20 mM potassium phosphate, 0.1 M NaCl, pH 6.5). The components were mixed and the resulting reaction mixture was incubated at 37° C. for different times, including 2 h, 4 h, 8 h, 24 h, and 48 h. Purification of sialylated antibody was performed as in Example 13.

To analyze the degree of sialylation, 124 µL denaturing buffer (6 M Guanidinium chloride in water) and 30 µL TCEP (=tris(2-carboxyethyl)phosphine; 0.1 mM, diluted in denaturing buffer) were added to 76 µL (corresponding to 250 µg IgG1 MAB) and the sample was incubated at 37° C. for 1 h. After that the sample was buffered in electrospray medium [20% ACN (=acetonitrile), 1% FA (=formamide)] using pre-equilibrated Illustra™ Nap5-Columns (GE-Healthcare). Subsequently the sample was analyzed by electrospray ionization mass spectrometry, and the content of G2+0SA, G2+1SA and G2+2SA N-glycans was determined. A Synapt G2 HDMS device (Waters UK) was used, the software used was MassLynx V 4.1.

Example 13

Purification of Sialylated IgG1 MAB

To remove sialyltransferase and CMP-NANA from the incubated sialylation reaction mixture of Example 12, incubated IgG1 MAB was purified using Protein A. The reaction mixture was applied to a Protein A column equilibrated with 25 mM Tris, 25 mM NaCl, 5 mM EDTA (=ethylenediaminetetraacetic acid), pH 7. The column was washed with 25 mM Tris, 25 mM NaCl, 500 mM TMAC (=tetramethylammonium chloride), 5 mM EDTA pH 5.0 and then with 25 mM Tris, 25 mM NaCl, 5 mM EDTA pH 7.1. IgG1 MAB was eluted with 25 mM Na-Citrate. To avoid spontaneous desilylation at low pH, the pH was adjusted to pH 7.0 using 1 M Tris pH 9.0. Using this procedure sialylated IgG1 MAB was obtained in pure form, with a typical yield of 12 mg.

Example 14

Sialidase Activity of Δ89 hST6Gal-I on IgG1 MAB in the Presence and Absence of CMP Cytidine monophosphate (5'-CMP, =CMP) is a product of the reaction catalyzed by sialyltransferase enzymes, generated in the course of the glycosyltransferase reaction from the co-substrate CMP-NANA. With incubation time of a sialylation reaction CMP accumulates in the reaction mixture. To demonstrate that the inherent sialidase activity is CMP-dependent, highly sialylated IgG1 monoclonal antibody IgG1 MAB G2+2SA was prepared by incubation with Δ89 hST6Gal-I in the presence of CMP-NANA, as described in Example 12, and purified as described in Example 13.

To an amount of 1,250 µg (in 194 µL) highly sialylated IgG1 MAB according to Example 12 with an incubation period for sialylation of 8 h, 125 µg sialyltransferase variant (30 µg/300 µg IgG1 MAB) was added.

Different N-terminally truncated hST6Gal-I enzyme variants were tested for CMP-dependent sialidase activity:
  Δ89 hST6Gal-I (Example 9)
  Δ108 hST6Gal-I (Example 9)
  Δ57 hST3Gal-I (obtained from R&D Systems)

Four different experiments were made using Δ89 hST6Gal-I (16.8 µL with 125 µg), Δ108 hST6Gal-I (17.3 µL with 125 µg), Δ57 hST3Gal-I (20.1 µL with 125 µg) and a negative control (no enzyme, 20.1 µL ultrapure water). The enzymes were tested for sialidase activity in the absence and presence of CMP (10-fold excess based on molarity). The concentrations were as shown as follows:
  Δ89 hST6Gal-I (16.8 µL with 125 µg): 11.8 µg CMP (c=0.5 mg/mL 23.6 µL)
  Δ108 hST6Gal-I (17.3 µL with 125 µg): 12.3 µg CMP (c=0.5 mg/mL 24.5 µL)
  Δ57 hST3Gal-I (20.1 µL with 125 µg): 12.3 µg CMP (c=0.5 mg/mL 24.5 µL)
  Negative control (no enzyme): 12.3 µg CMP (c=0.5 mg/mL 24.5 µL)

The samples were incubated at 37° C. in 20 mM sodium citrate, 35 mM Tris pH 6.5. Aliquots were taken as samples after different incubation times, and were analyzed.

To analyze the degree of sialylation of IgG1 MAB in the samples, 124 µL denaturing buffer (6 M Guanidinium chloride in water) and 30 µL TCEP (=tris(2-carboxyethyl)phosphine; 0.1 mM, diluted in denaturing buffer) were added to 76 µL (corresponding to 250 µg IgG1 MAB) and the sample was incubated at 37° C. for 1 h. After that the sample was buffered in electrospray medium (20% ACN (=acetonitrile), 1% FA (=formamide)) using pre-equilibrated Illustra™ Nap5-Columns (GE-Healthcare). Subsequently the sample was analyzed by electrospray ionization mass spectrometry and the content of G2+0SA, G2+1SA and G2+2SA N-glycans was determined. A Synapt G2 HDMS device (Waters UK) was used, the software used was MassLynx V 4.1.

Figure 7:
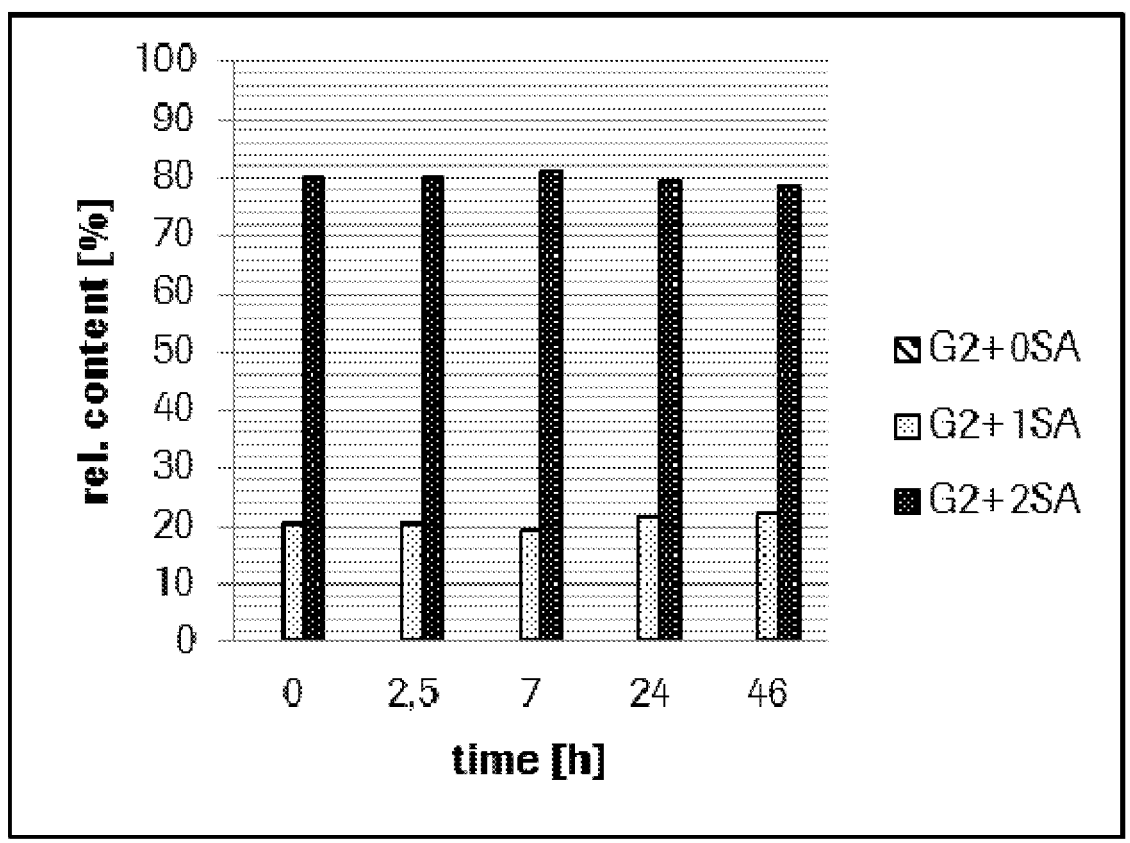
FIG. 7 CMP-dependent sialidase activity of Δ89 hST6Gal-I: Incubation of purified IgG1 MAB G2+2SA with Δ89 hST6Gal-I in the absence of CMP. The relative content of antibodies with glycans with terminal galactose residues (G2+0SA), monosialylated glycan (G2+1SA) and disialylated glycan (G2+2SA) are shown for different time points.
Figure 8:
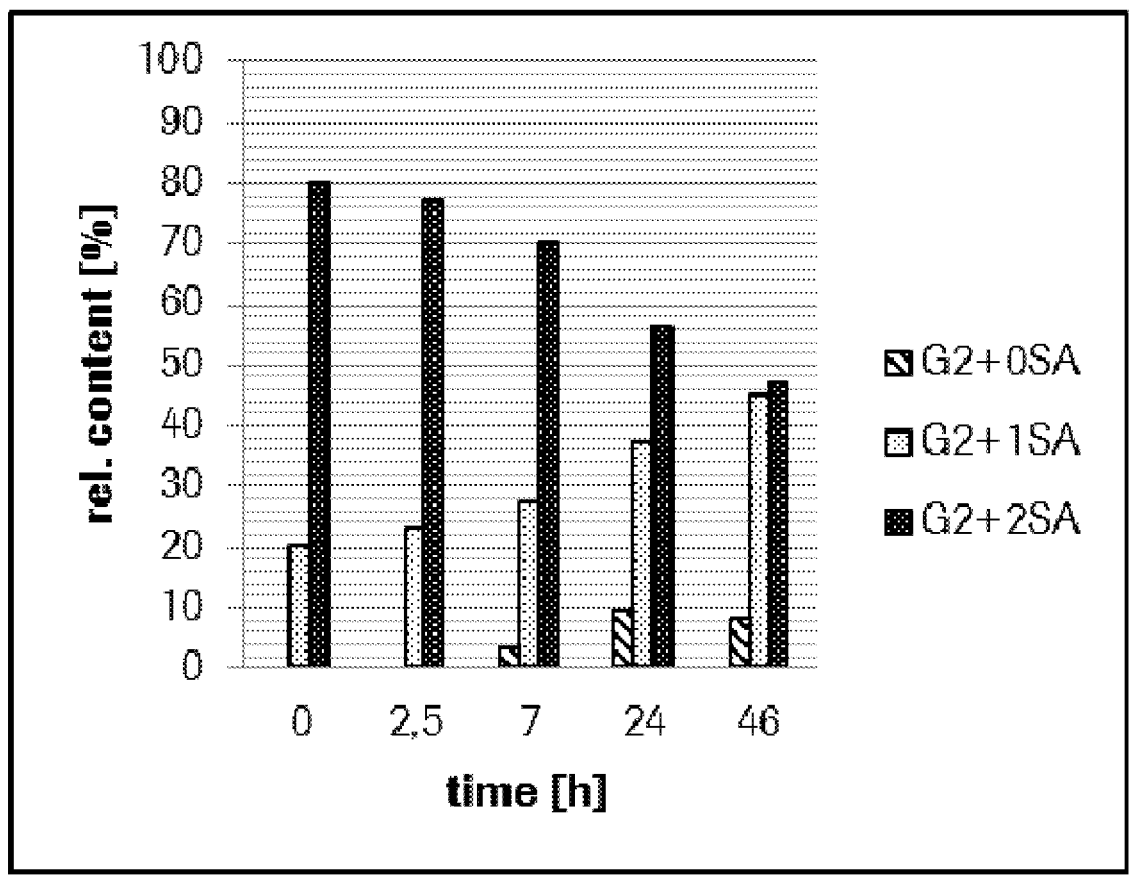
FIG. 8 CMP-dependent sialidase activity of Δ89 hST6Gal-I: Incubation of purified IgG1 MAB G2+2SA with Δ89 hST6Gal-I in the presence of CMP. The relative content of antibodies with glycans with terminal galactose residues (G2+0SA), monosialylated glycan (G2+1SA) and disialylated glycan (G2+2SA) are shown for different time points.
Figure 9:
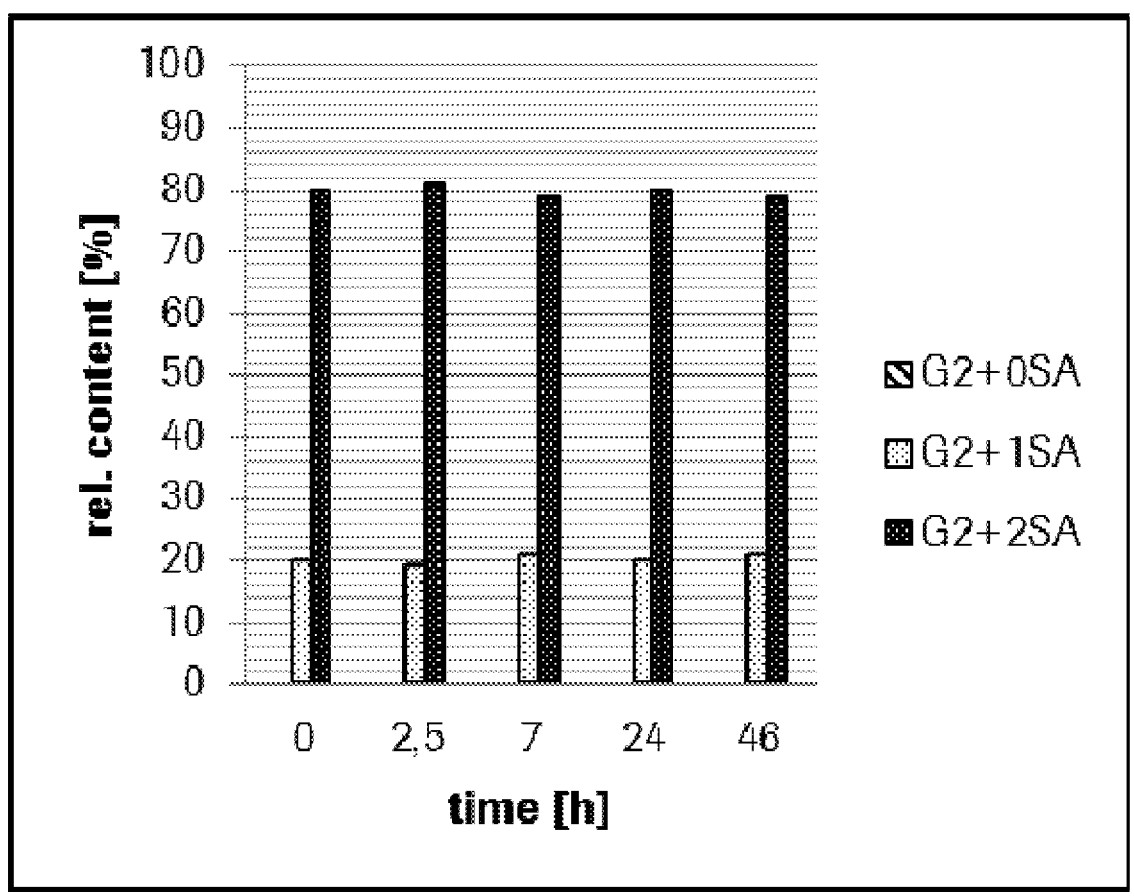
FIG. 9 CMP-dependent sialidase activity of Δ89 hST6Gal-I: Incubation of purified IgG1 MAB G2+2SA with Δ108 hST6Gal-I in the presence of CMP. The relative content of antibodies with glycans with terminal galactose residues (G2+0SA), monosialylated glycan (G2+1SA) and disialylated glycan (G2+2SA) are shown for different time points.
Figure 10:
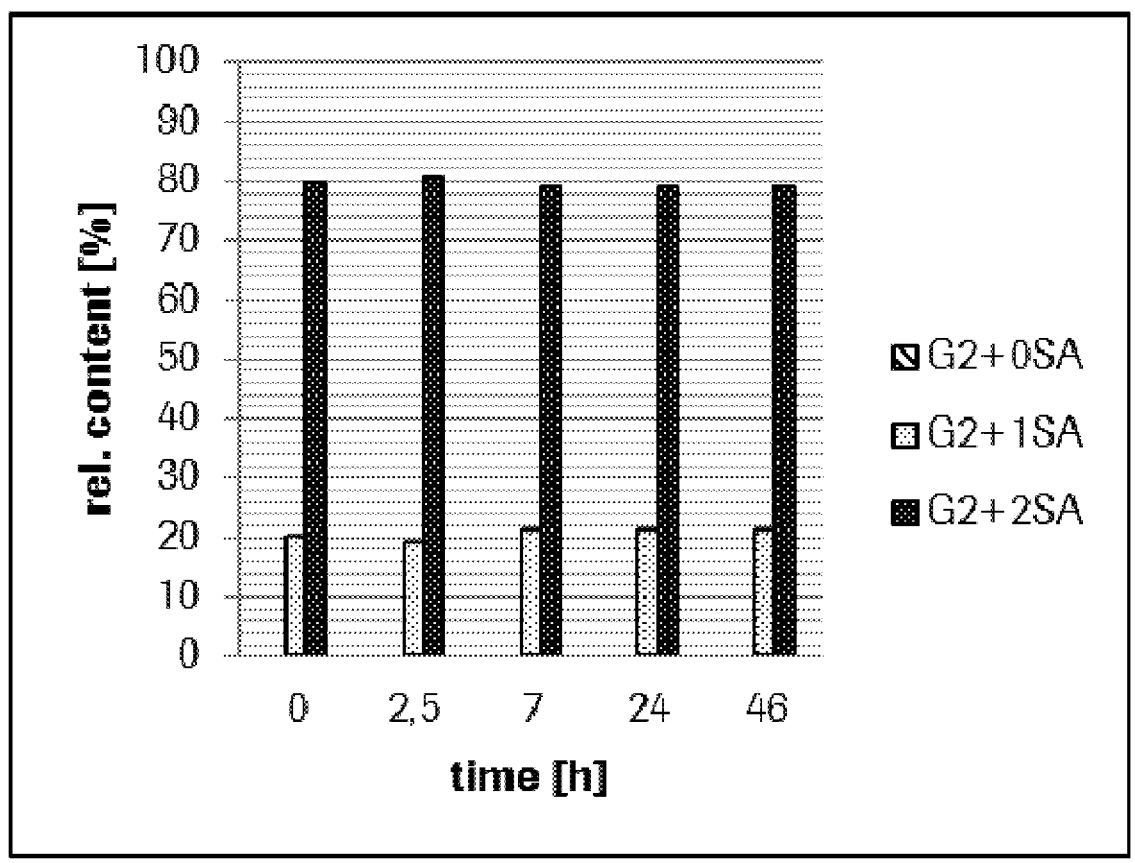
FIG. 10 CMP-dependent sialidase activity of Δ89 hST6Gal-I: Incubation of purified IgG1 MAB G2+2SA with delta57ST3-Gal-I in the presence of CMP. The relative content of antibodies with glycans with terminal galactose residues (G2+0SA), monosialylated glycan (G2+1SA) and disialylated glycan (G2+2SA) are shown for different time points.
Figure 11:
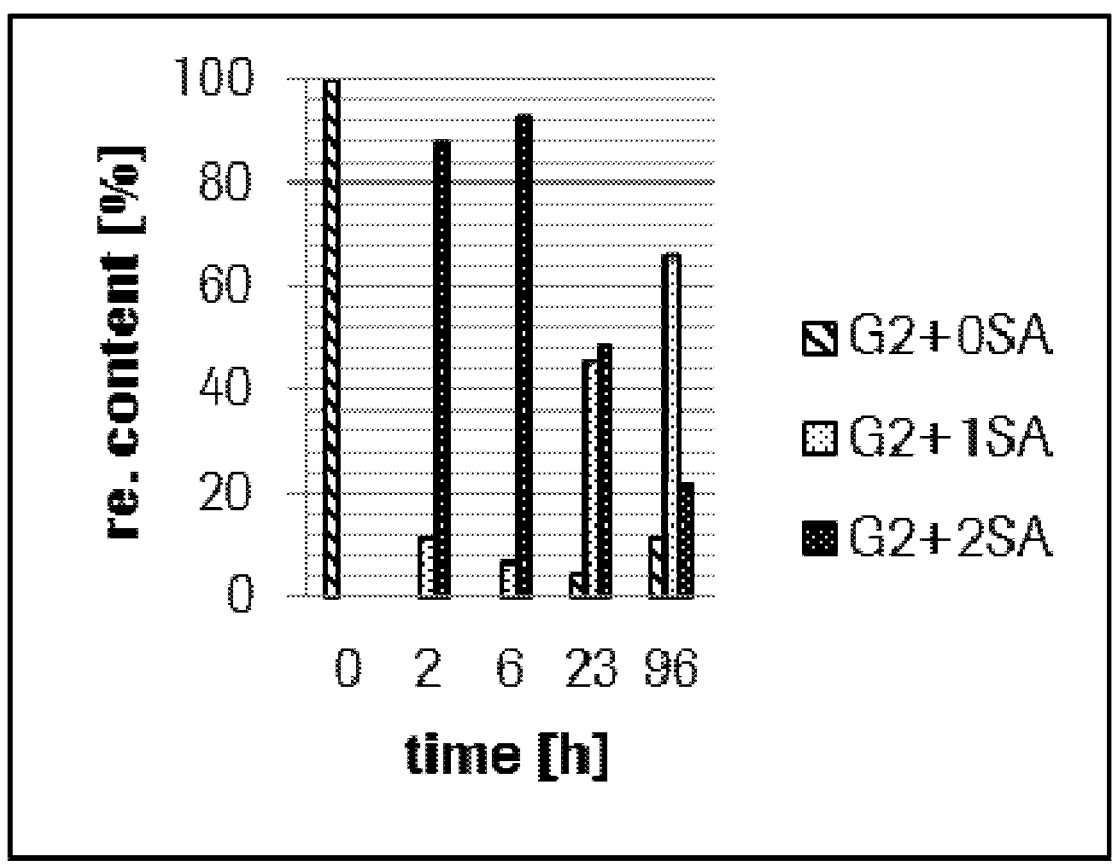
FIG. 11 Sialylation of IgG4 MAB with Δ89 hST6Gal-I in the absence or presence of 5'-nucleotidase CD73 in the sialylation reaction mixture. The relative content of antibodies with glycans with just terminal galactose residues (G2+0SA), monosialylated glycan (G2+1SA) and disialylated glycan (G2+2SA) is shown. The amount of 5'-nucleotidase used was 0-0.5 µg. Negative control: 0 µg 5'-nucleotidase CD73.
Figure 12:
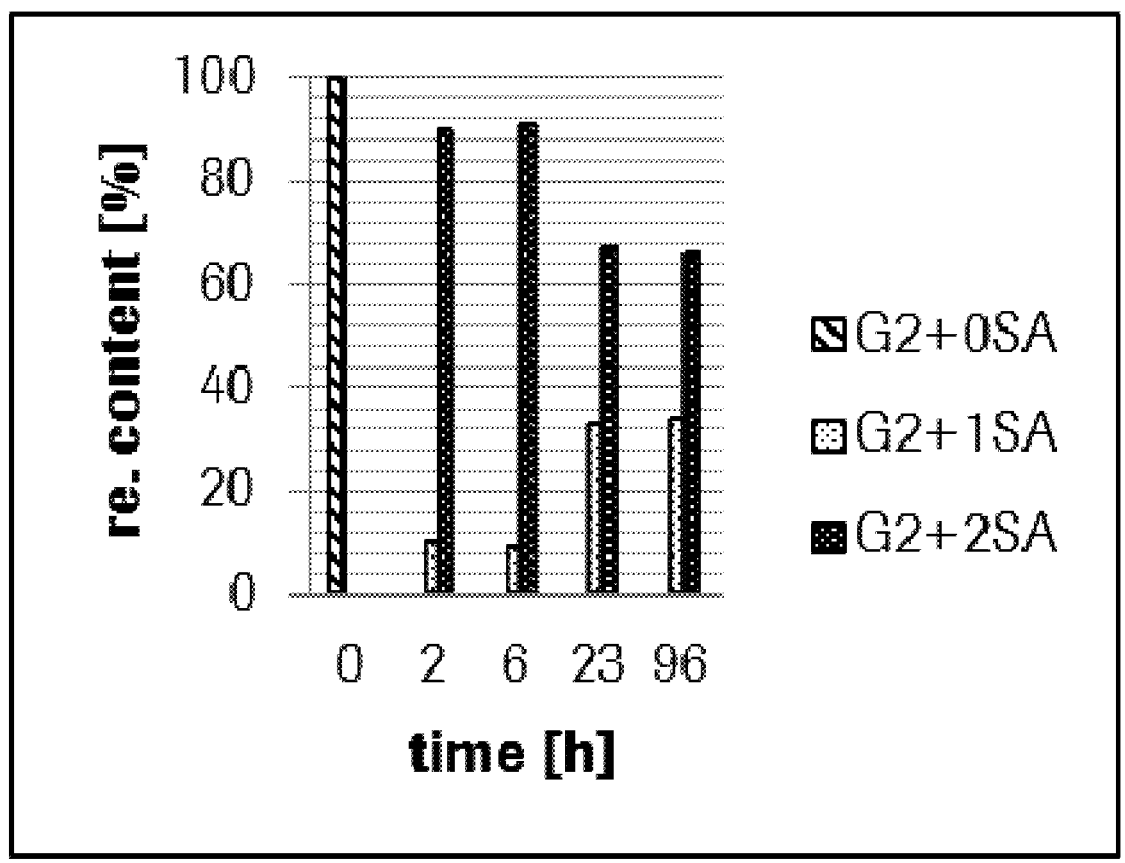
FIG. 12 Sialylation of IgG4 MAB with Δ89 hST6Gal-I in the absence or presence of 5'-nucleotidase CD73 in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 0.1 µg 5'-nucleotidase CD73.
Figure 13:
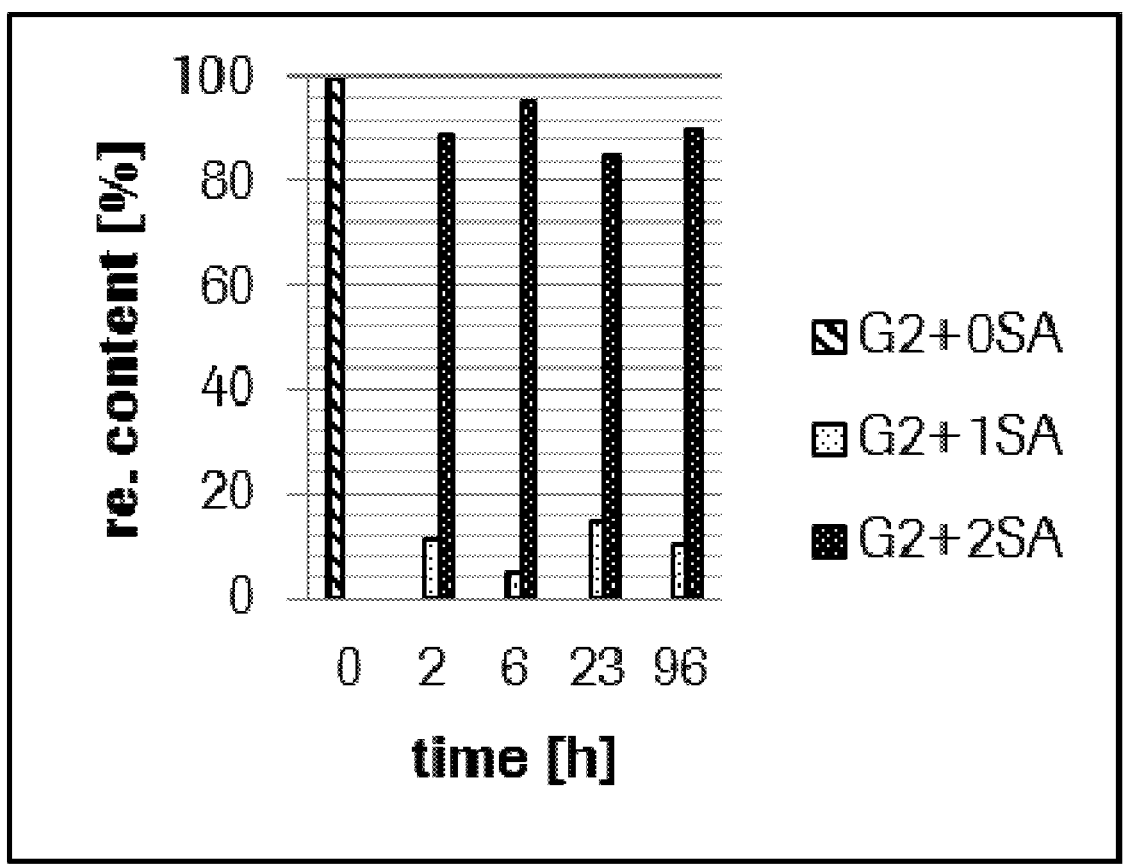
FIG. 13 Sialylation of IgG4 MAB with Δ89 hST6Gal-I in the absence or presence of 5'-nucleotidase CD73 in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 0.25 µg 5'-nucleotidase CD73.
Figure 14:
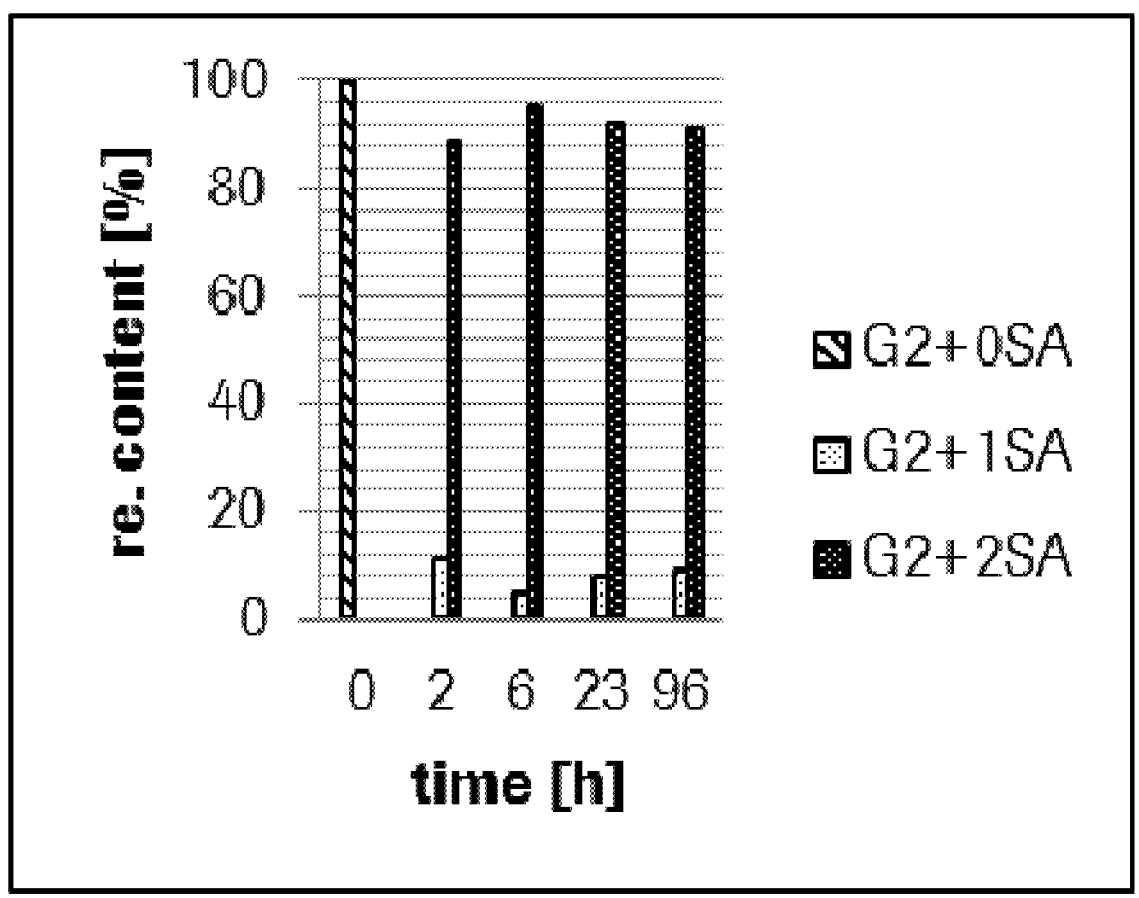
FIG. 14 Sialylation of IgG4 MAB with Δ89 hST6Gal-I in the absence or presence of 5'-nucleotidase CD73 in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 0.5 µg 5'-nucleotidase CD73.
Figure 15:
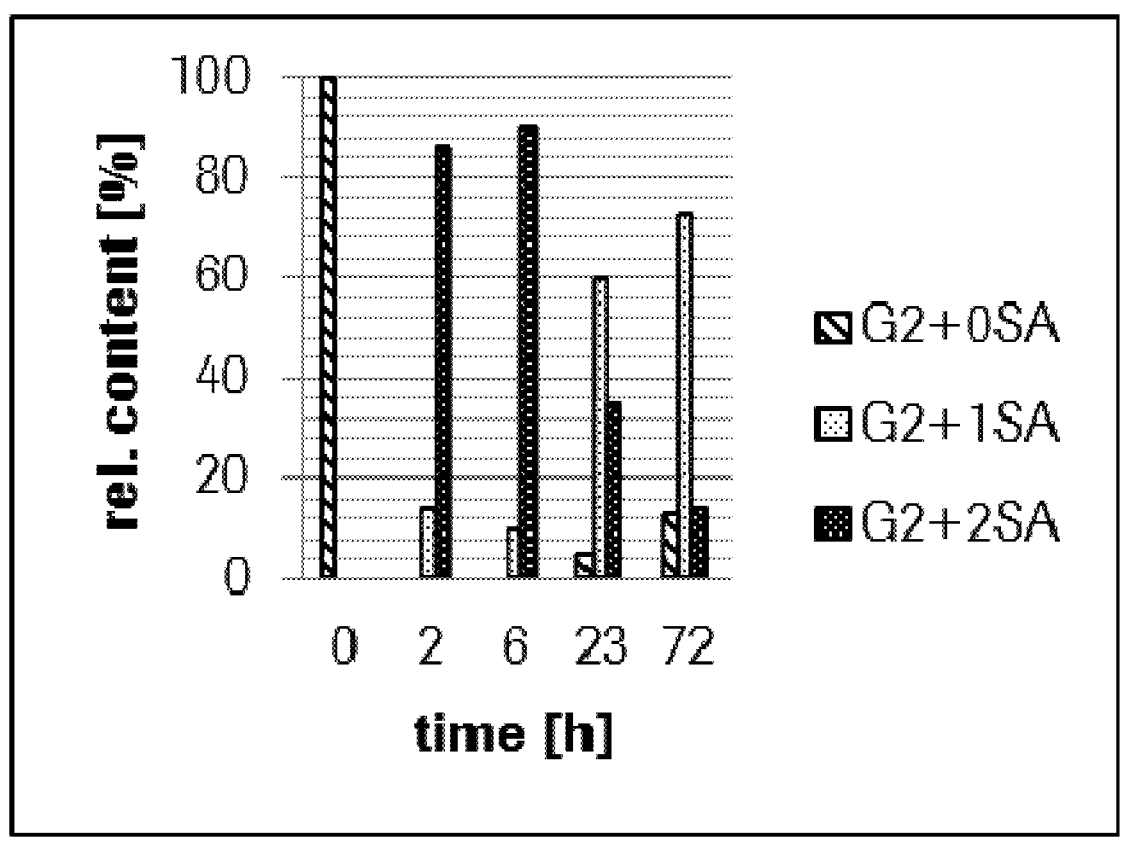
FIG. 15 Sialylation of IgG4 MAB with Δ89 hST6Gal-I in the absence or presence of alkaline phosphatase in the sialylation reaction mixture. The relative content of antibodies with glycans with just terminal galactose residues (G2+0SA), monosialylated glycan (G2+1SA) and disialylated glycan (G2+2SA) is shown. The amount of 5'-nucleotidase used was 0-100 µg. Negative control: 0 µg alkaline phosphatase.
Figure 16:
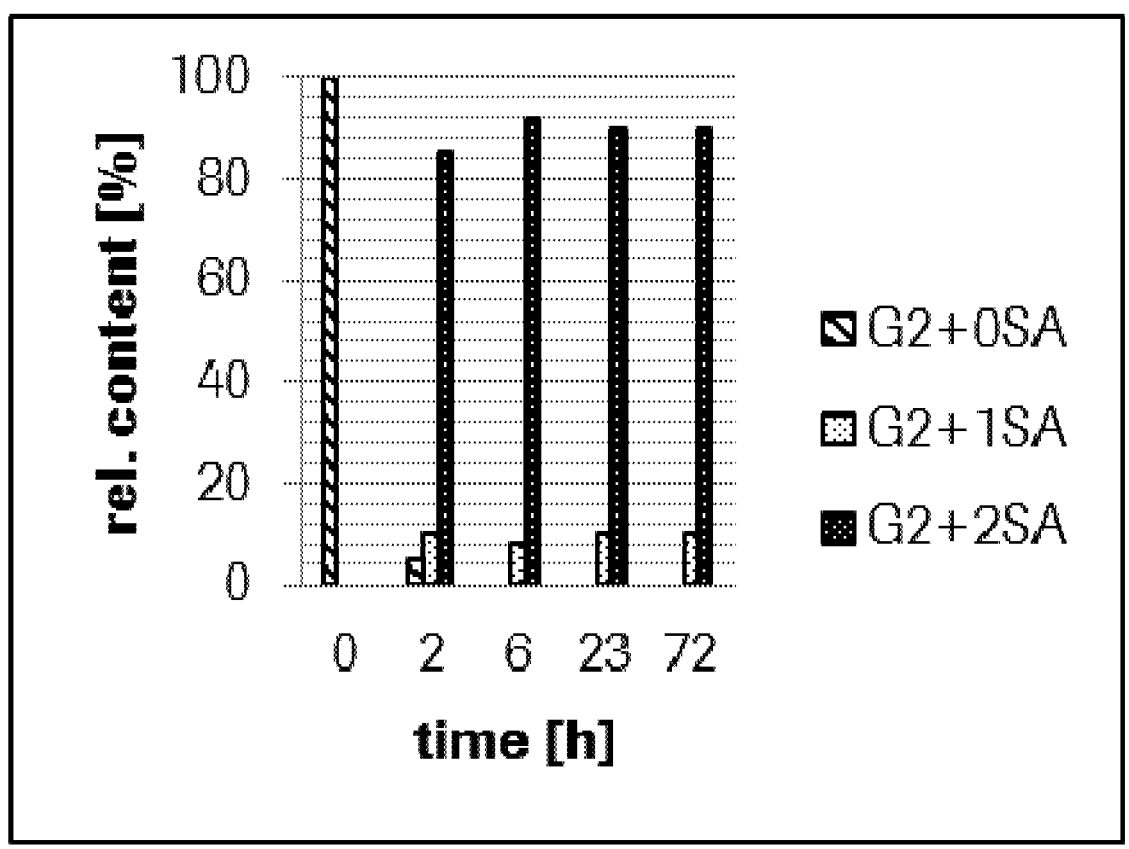
FIG. 16 Sialylation of IgG4 MAB with Δ89 hST6Gal-I in the absence or presence of alkaline phosphatase in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 1 µg alkaline phosphatase.
Figure 17:
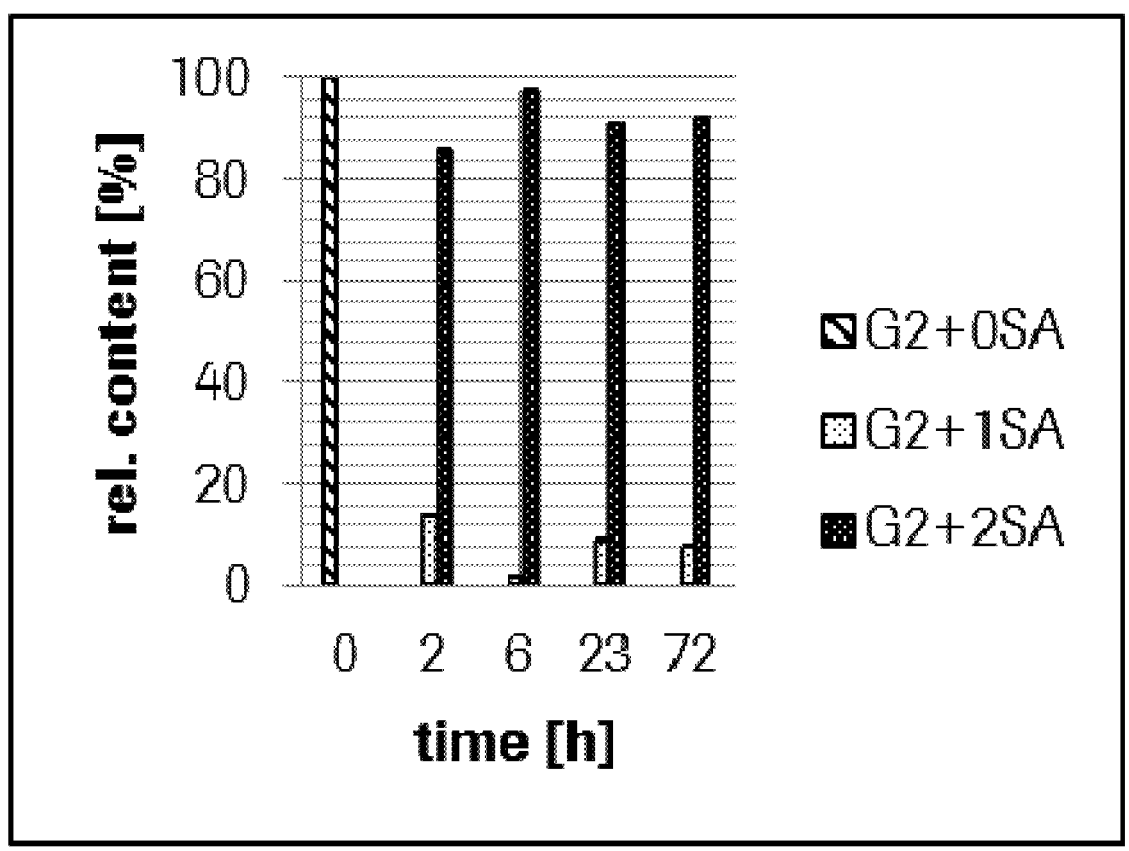
FIG. 17 Sialylation of IgG4 MAB with Δ89 hST6Gal-I in the absence or presence of alkaline phosphatase in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 5 µg alkaline phosphatase.
Figure 18:
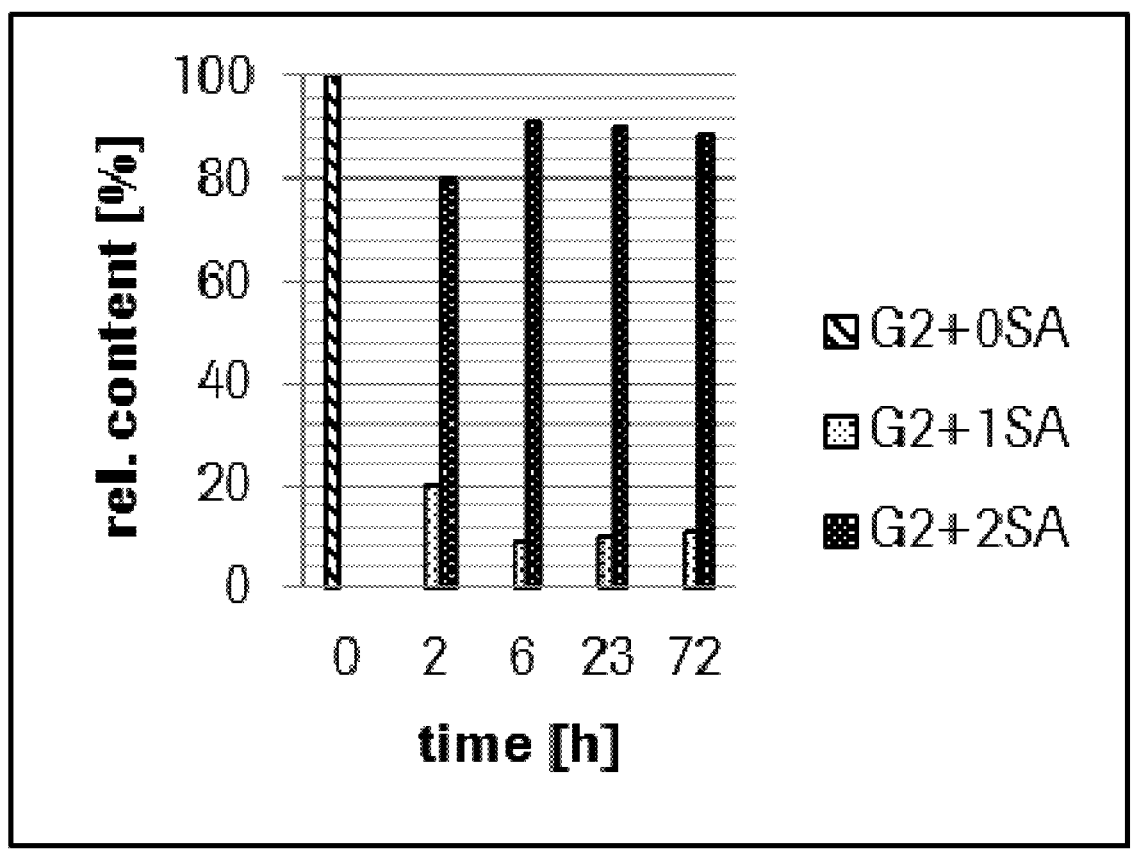
FIG. 18 Sialylation of IgG4 MAB with Δ89 hST6Gal-I in the absence or presence of alkaline phosphatase in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 10 µg alkaline phosphatase.
Figure 19:
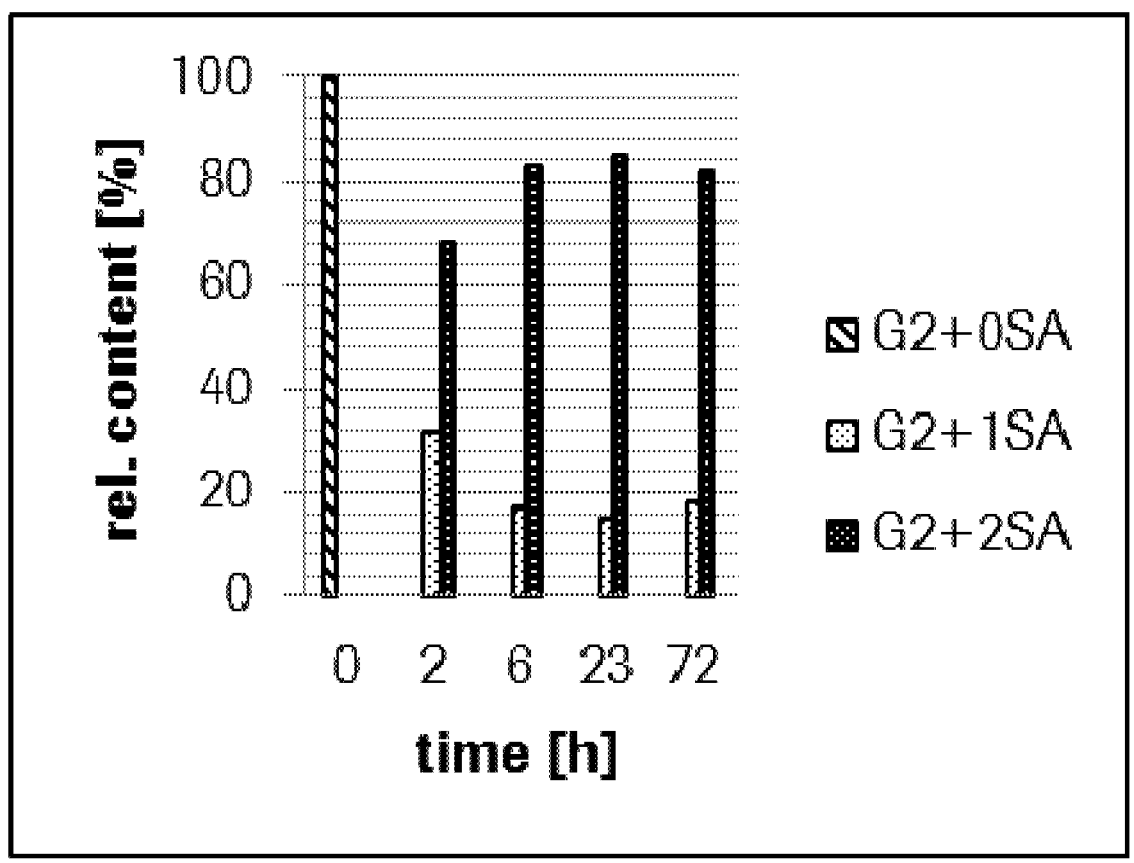
FIG. 19 Sialylation of IgG4 MAB with Δ89 hST6Gal-I in the absence or presence of alkaline phosphatase in the sialylation reaction mixture. The relative content of antibodies with glycans with just terminal galactose residues (G2+0SA), monosialylated glycan (G2+1SA) and disialylated glycan (G2+2SA) is shown. Sialylation reaction mixture with 100 µg alkaline phosphatase.

The results are shown in FIGS. 7-10. In the reaction mixture without CMP no degradation of G2+2SA was observed even after incubation for 46 h (FIG. 7). Whereas in the presence of CMP a degradation of G2+2SA was measured accompanied by an increase of the content of G2+1SA (FIG. 8). Under the conditions described above Δ89 hST6Gal-I showed a CMP-dependent sialidase activity, whereas Δ108 hST6Gal-I (FIG. 9) and Δ57 ST3Gal-I (FIG. 10) did not show any sialidase activity in the presence of CMP. In the latter case this is noted that the enzyme is specific for 2-3 glycosidic bonds Example 15

Sialylation of IgG4 MAB Using Δ89 hST6Gal-I in the Presence of Phosphatase Enzymatic Activity Suppression of CMP-dependent sialidase activity of Δ89 hST6Gal-I was studied by continuous removal of CMP formed during the reaction.

In the experiments the enzymes (i) 5'-nucleotidase (EC 3.1.3.5) having a wide specificity for 5'-nucleotides, and (ii) alkaline phosphatase (EC 3.1.3.1) (both provided by commercial suppliers) were used. The particular 5'-nucleotidase used here is also known as ecto-5'-nucleotidase or CD73 (Cluster of Differentiation 73), in humans encoded by the NT5E gene. Both enzymes dephosphorylate CMP, i.e. catalyze hydrolysis of the phosphoester bond in CMP. In the experiments of this Example the enzymes were used to degrade CMP generated by the sialyltransferase reaction from the co-substrate CMP-NANA. In the absence of CMP no intrinsic sialidase activity of Δ89 hST6Gal-I was observed.

To 1,000 µg IgG4 MAB (184 µL) 500 µg CMP-NANA (3 mg/mL, 166.7 µL), 100 µg Δ89 hST6Gal-I (13.4 µL, 30 µg/300 µg IgG4 MAB) and different amounts of nucleotidase (Nu) and alkaline phosphatase (AP) were added. As $Zn^{2+}$ ions are essential for the activity of AP, these were added to a final concentration of 0.1 mM). The buffer used was 20 mM sodium acetate/Tris, pH 6.5.

Different amounts of the enzymes were added to the reaction mixtures to study the effect of the dephosphorylating enzymes:
  1) 5'-nucleotidase CD73 was used in a concentration of 0.1 µg/µL. To the reactions 0.10 µg, 0.25 µg and 0.50 µg were added.
  2) Alkaline phosphatase (AP) was used in a concentration of 1 µL and 10 µg/µL. To the reactions 1 µg, 5 µg, 10 µg and 100 µg were added.

After addition of the respective amounts of enzymes the samples were incubated at 37° C. Samples were taken at several time points to control the degree of sialylation. Therefore 110 µL denaturing buffer (6 M Guanidinium chloride) and 30 µL TCEP (0.1 mM, diluted in denaturing buffer) were added to 90 µL of the sample (about 250 µg IgG4 MAB) and the sample was incubated at 37° C. for 1 h. After that the sample was buffered in electrospray medium [20% ACN (=acetonitrile), 1% FA (=formamide)] using pre-equilibrated Illustra™ Nap5-Columns (GE-Healthcare). Then the sample was analyzed by electrospray ionization mass spectrometry, and the content of G2+0SA, G2+1SA and G2+2SA N-glycans was determined. A Synapt G2 HDMS device (Waters UK) were used, the software used was MassLynx V 4.1.

Results for sialylation of IgG4 MAB by Δ89 hST6Gal-I in the absence or presence of 5'-nucleotidase CD73 are depicted in FIGS. 11-14; and results for sialylation of IgG4

MAB by Δ89 hST6Gal-I in the absence or presence of alkaline phosphatase are depicted in FIGS. 15-19. As it turned out, introducing a phosphatase activity capable of hydrolyzing the phosphoester bond in 5'-CMP effectively reduced CMP-mediated sialidase activity and promoted sialyltransferase activity.

The invention claimed is:

1. An aqueous composition comprising:
   (a) a soluble human β-galactoside-α-2,6-sialyltransferase I comprising the amino acid motif from position 90 to position 108 in SEQ ID NO:1;
   (b) a cytidine-5'-monophospho-N-acetylneuraminic acid;
   (c) a glycosylated target molecule selected from the group consisting of a glycoprotein and a glycolipid, the target molecule comprising one or more antenna(e), at least one antenna having as a terminal structure a β-D-galactosyl-1,4-N-acetyl-β-D-glucosamine moiety with a hydroxyl group at the C6 position in the galactosyl residue;
   (d) an aqueous solution permitting glycosyltransferase enzymatic activity comprising a buffer salt;
   wherein the aqueous composition further comprises an enzyme selected from the group consisting of an alkaline phosphatase, an acid phosphatase, and a 5' nucleotidase capable of hydrolyzing the phosphoester bond in 5'-cytidine-monophosphate under conditions permitting glycosyltransferase enzymatic activity.

* * * * *

SEQUENCE LISTING

```
<160> NUMBER OF SEQ ID NOS: 7

<210> SEQ ID NO 1
<211> LENGTH: 406
<212> TYPE: PRT
<213> ORGANISM: Homo sapiens
<220> FEATURE:
<221> NAME/KEY: MISC_FEATURE
<223> OTHER INFORMATION: hST6-Gal-I WT polypeptide

<400> SEQUENCE: 1

Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Lys Gly
                20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
                115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
                180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320
```

```
Pro Ser Ser Gly Met Leu Gly Ile Ile Met Met Thr Leu Cys Asp
            325                 330                 335

Gln Val Asp Ile Tyr Glu Phe Leu Pro Ser Lys Arg Lys Thr Asp Val
        340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
370                 375                 380

Gly Thr Asp Glu Asp Ile Tyr Leu Leu Gly Lys Ala Thr Leu Pro Gly
385                 390                 395                 400

Phe Arg Thr Ile His Cys
            405
```

<210> SEQ ID NO 2
<211> LENGTH: 317
<212> TYPE: PRT
<213> ORGANISM: Artificial Sequence
<220> FEATURE:
<223> OTHER INFORMATION: delta89 truncation variant of hST6Gal-I

<400> SEQUENCE: 2

```
Glu Ala Ser Phe Gln Val Trp Asn Lys Asp Ser Ser Ser Lys Asn Leu
1               5                   10                  15

Ile Pro Arg Leu Gln Lys Ile Trp Lys Asn Tyr Leu Ser Met Asn Lys
            20                  25                  30

Tyr Lys Val Ser Tyr Lys Gly Pro Gly Pro Gly Ile Lys Phe Ser Ala
        35                  40                  45

Glu Ala Leu Arg Cys His Leu Arg Asp His Val Asn Val Ser Met Val
50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
            85                  90                  95

Val Val Ser Ser Ala Gly Ser Leu Lys Ser Ser Gln Leu Gly Arg Glu
            100                 105                 110

Ile Asp Asp His Asp Ala Val Leu Arg Phe Asn Gly Ala Pro Thr Ala
        115                 120                 125

Asn Phe Gln Gln Asp Val Gly Thr Lys Thr Thr Ile Arg Leu Met Asn
130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
            165                 170                 175

Ile Pro Lys Trp Tyr Gln Asn Pro Asp Tyr Asn Phe Phe Asn Asn Tyr
        180                 185                 190

Lys Thr Tyr Arg Lys Leu His Pro Asn Gln Pro Phe Tyr Ile Leu Lys
        195                 200                 205

Pro Gln Met Pro Trp Glu Leu Trp Asp Ile Leu Gln Glu Ile Ser Pro
210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
            245                 250                 255

Ser Lys Arg Lys Thr Asp Val Cys Tyr Tyr Tyr Gln Lys Phe Phe Asp
            260                 265                 270
```

```
Ser Ala Cys Thr Met Gly Ala Tyr His Pro Leu Leu Tyr Glu Lys Asn
        275                 280                 285

Leu Val Lys His Leu Asn Gln Gly Thr Asp Glu Asp Ile Tyr Leu Leu
        290                 295                 300

Gly Lys Ala Thr Leu Pro Gly Phe Arg Thr Ile His Cys
305                 310                 315

<210> SEQ ID NO 3
<211> LENGTH: 1054
<212> TYPE: DNA
<213> ORGANISM: Artificial Sequence
<220> FEATURE:
<223> OTHER INFORMATION: Expression construct Epo-AP-delta89 ST6
      (90-406)
<220> FEATURE:
<221> NAME/KEY: misc_recomb
<222> LOCATION: (1)..(6)
<223> OTHER INFORMATION: Sal-I restriction site
<220> FEATURE:
<221> NAME/KEY: CDS
<222> LOCATION: (8)..(1048)
<223> OTHER INFORMATION: nucleic acid sequence encoding a fusion
      polypeptide of delta89 hST6-Gal-I, N-terminally fused to the Epo
      leader peptide and containing an "AP" joining sequence
<220> FEATURE:
<221> NAME/KEY: misc_feature
<222> LOCATION: (95)..(1048)
<223> OTHER INFORMATION: portion ot the nucleic acid sequence encoding
      the delta89 hST6-Gal-I portion of the fusion polypeptide
<220> FEATURE:
<221> NAME/KEY: misc_recomb
<222> LOCATION: (1049)..(1054)
<223> OTHER INFORMATION: BamH-I restriction site

<400> SEQUENCE: 3 gtcgacc atg ggc gtg cac gaa tgt cct gcc tgg ctg tgg ctg ctg ctg       49
        Met Gly Val His Glu Cys Pro Ala Trp Leu Trp Leu Leu Leu
        1               5                   10 agc ctg ctg tct ctg cct ctg gga ctg cct gtg ctg ggc gcc cct gaa       97
Ser Leu Leu Ser Leu Pro Leu Gly Leu Pro Val Leu Gly Ala Pro Glu
15                  20                  25                  30 gcc tct ttc cag gtg tgg aac aag gac agc agc tcc aag aac ctg atc      145
Ala Ser Phe Gln Val Trp Asn Lys Asp Ser Ser Ser Lys Asn Leu Ile
                35                  40                  45 ccc cgg ctg cag aag atc tgg aag aac tac ctg agc atg aac aag tac      193
Pro Arg Leu Gln Lys Ile Trp Lys Asn Tyr Leu Ser Met Asn Lys Tyr
            50                  55                  60 aag gtg tcc tac aag ggc cct ggc cct ggc atc aag ttt agc gcc gag      241
Lys Val Ser Tyr Lys Gly Pro Gly Pro Gly Ile Lys Phe Ser Ala Glu
        65                  70                  75 gcc ctg aga tgc cac ctg agg gat cac gtg aac gtg tcc atg gtg gaa      289
Ala Leu Arg Cys His Leu Arg Asp His Val Asn Val Ser Met Val Glu
80                  85                  90 gtg acc gac ttc cca ttc aac acc agc gag tgg gag ggc tac ctg ccc      337
Val Thr Asp Phe Pro Phe Asn Thr Ser Glu Trp Glu Gly Tyr Leu Pro
95                  100                 105                 110 aaa gag agc atc cgg acc aaa gcc ggc cct tgg gga aga tgt gcc gtg      385
Lys Glu Ser Ile Arg Thr Lys Ala Gly Pro Trp Gly Arg Cys Ala Val
                115                 120                 125 gtg tct agc gcc ggc agc ctg aag agt agc cag ctg ggc aga gag atc      433
Val Ser Ser Ala Gly Ser Leu Lys Ser Ser Gln Leu Gly Arg Glu Ile
            130                 135                 140 gac gac cac gac gcc gtg ctg cgg ttc aat ggc gct ccc acc gcc aac      481
Asp Asp His Asp Ala Val Leu Arg Phe Asn Gly Ala Pro Thr Ala Asn
        145                 150                 155
```

```
ttc cag cag gac gtg ggc acc aag acc acc atc cgg ctg atg aac tcc     529
Phe Gln Gln Asp Val Gly Thr Lys Thr Thr Ile Arg Leu Met Asn Ser
    160                 165                 170 cag ctc gtg aca acc gag aag cgg ttc ctg aag gac agc ctg tac aac     577
Gln Leu Val Thr Thr Glu Lys Arg Phe Leu Lys Asp Ser Leu Tyr Asn
175                 180                 185                 190 gag ggc atc ctg atc gtg tgg gac ccc agc gtg tac cac agc gac atc     625
Glu Gly Ile Leu Ile Val Trp Asp Pro Ser Val Tyr His Ser Asp Ile
                195                 200                 205 ccc aag tgg tat cag aac ccc gac tac aac ttc ttc aac aac tac aag     673
Pro Lys Trp Tyr Gln Asn Pro Asp Tyr Asn Phe Phe Asn Asn Tyr Lys
            210                 215                 220 acc tac cgg aag ctg cac ccc aac cag ccc ttc tac atc ctg aag ccc     721
Thr Tyr Arg Lys Leu His Pro Asn Gln Pro Phe Tyr Ile Leu Lys Pro
        225                 230                 235 cag atg ccc tgg gag ctg tgg gac att ctg cag gaa atc agc ccc gaa     769
Gln Met Pro Trp Glu Leu Trp Asp Ile Leu Gln Glu Ile Ser Pro Glu
    240                 245                 250 gag atc cag ccc aac ccc cct agc tct ggc atg ctg ggc atc att atc     817
Glu Ile Gln Pro Asn Pro Pro Ser Ser Gly Met Leu Gly Ile Ile Ile
255                 260                 265                 270 atg atg acc ctg tgc gac cag gtg gac atc tac gag ttt ctg ccc tcc     865
Met Met Thr Leu Cys Asp Gln Val Asp Ile Tyr Glu Phe Leu Pro Ser
                275                 280                 285 aag aga aag acc gac gtg tgc tac tac tac cag aag ttc ttc gac agc     913
Lys Arg Lys Thr Asp Val Cys Tyr Tyr Tyr Gln Lys Phe Phe Asp Ser
            290                 295                 300 gcc tgc acc atg gga gcc tac cac cct ctg ctg tac gag aag aac ctc     961
Ala Cys Thr Met Gly Ala Tyr His Pro Leu Leu Tyr Glu Lys Asn Leu
        305                 310                 315 gtg aag cac ctg aac cag ggc acc gac gag gat atc tac ctg ctg ggc    1009
Val Lys His Leu Asn Gln Gly Thr Asp Glu Asp Ile Tyr Leu Leu Gly
    320                 325                 330 aag gcc acc ctg ccc ggc ttc aga acc atc cac tgc tga ggatcc         1054
Lys Ala Thr Leu Pro Gly Phe Arg Thr Ile His Cys
335                 340                 345
```

<210> SEQ ID NO 4
<211> LENGTH: 346
<212> TYPE: PRT
<213> ORGANISM: Artificial Sequence
<220> FEATURE:
<223> OTHER INFORMATION: Synthetic Construct

<400> SEQUENCE: 4

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Glu Ala Ser
            20                  25                  30

Phe Gln Val Trp Asn Lys Asp Ser Ser Lys Asn Leu Ile Pro Arg
        35                  40                  45

Leu Gln Lys Ile Trp Lys Asn Tyr Leu Ser Met Asn Lys Tyr Lys Val
    50                  55                  60

Ser Tyr Lys Gly Pro Gly Pro Gly Ile Lys Phe Ser Ala Glu Ala Leu
65                  70                  75                  80

Arg Cys His Leu Arg Asp His Val Asn Val Ser Met Val Glu Val Thr
                85                  90                  95

Asp Phe Pro Phe Asn Thr Ser Glu Trp Glu Gly Tyr Leu Pro Lys Glu
            100                 105                 110
```

```
Ser Ile Arg Thr Lys Ala Gly Pro Trp Gly Arg Cys Ala Val Val Ser
            115                 120                 125

Ser Ala Gly Ser Leu Lys Ser Ser Gln Leu Gly Arg Glu Ile Asp Asp
        130                 135                 140

His Asp Ala Val Leu Arg Phe Asn Gly Ala Pro Thr Ala Asn Phe Gln
145                 150                 155                 160

Gln Asp Val Gly Thr Lys Thr Ile Arg Leu Met Asn Ser Gln Leu
                165                 170                 175

Val Thr Thr Glu Lys Arg Phe Leu Lys Asp Ser Leu Tyr Asn Glu Gly
            180                 185                 190

Ile Leu Ile Val Trp Asp Pro Ser Val Tyr His Ser Asp Ile Pro Lys
            195                 200                 205

Trp Tyr Gln Asn Pro Asp Tyr Asn Phe Phe Asn Asn Tyr Lys Thr Tyr
        210                 215                 220

Arg Lys Leu His Pro Asn Gln Pro Phe Tyr Ile Leu Lys Pro Gln Met
225                 230                 235                 240

Pro Trp Glu Leu Trp Asp Ile Leu Gln Glu Ile Ser Pro Glu Glu Ile
                245                 250                 255

Gln Pro Asn Pro Pro Ser Ser Gly Met Leu Gly Ile Ile Ile Met Met
            260                 265                 270

Thr Leu Cys Asp Gln Val Asp Ile Tyr Glu Phe Leu Pro Ser Lys Arg
        275                 280                 285

Lys Thr Asp Val Cys Tyr Tyr Tyr Gln Lys Phe Phe Asp Ser Ala Cys
        290                 295                 300

Thr Met Gly Ala Tyr His Pro Leu Leu Tyr Glu Lys Asn Leu Val Lys
305                 310                 315                 320

His Leu Asn Gln Gly Thr Asp Glu Asp Ile Tyr Leu Leu Gly Lys Ala
                325                 330                 335

Thr Leu Pro Gly Phe Arg Thr Ile His Cys
            340                 345

<210> SEQ ID NO 5
<211> LENGTH: 298
<212> TYPE: PRT
<213> ORGANISM: Artificial Sequence
<220> FEATURE:
<223> OTHER INFORMATION: delta108 truncation variant of hST6Gal-I

<400> SEQUENCE: 5

Leu Gln Lys Ile Trp Lys Asn Tyr Leu Ser Met Asn Lys Tyr Lys Val
1               5                   10                  15

Ser Tyr Lys Gly Pro Gly Pro Gly Ile Lys Phe Ser Ala Glu Ala Leu
            20                  25                  30

Arg Cys His Leu Arg Asp His Val Asn Val Ser Met Val Glu Val Thr
        35                  40                  45

Asp Phe Pro Phe Asn Thr Ser Glu Trp Glu Gly Tyr Leu Pro Lys Glu
    50                  55                  60

Ser Ile Arg Thr Lys Ala Gly Pro Trp Gly Arg Cys Ala Val Val Ser
65                  70                  75                  80

Ser Ala Gly Ser Leu Lys Ser Ser Gln Leu Gly Arg Glu Ile Asp Asp
                85                  90                  95

His Asp Ala Val Leu Arg Phe Asn Gly Ala Pro Thr Ala Asn Phe Gln
            100                 105                 110

Gln Asp Val Gly Thr Lys Thr Ile Arg Leu Met Asn Ser Gln Leu
        115                 120                 125
```

```
Val Thr Thr Glu Lys Arg Phe Leu Lys Asp Ser Leu Tyr Asn Glu Gly
    130                 135                 140

Ile Leu Ile Val Trp Asp Pro Ser Val Tyr His Ser Asp Ile Pro Lys
145                 150                 155                 160

Trp Tyr Gln Asn Pro Asp Tyr Asn Phe Phe Asn Asn Tyr Lys Thr Tyr
                165                 170                 175

Arg Lys Leu His Pro Asn Gln Pro Phe Tyr Ile Leu Lys Pro Gln Met
                180                 185                 190

Pro Trp Glu Leu Trp Asp Ile Leu Gln Glu Ile Ser Pro Glu Glu Ile
                195                 200                 205

Gln Pro Asn Pro Pro Ser Ser Gly Met Leu Gly Ile Ile Ile Met Met
    210                 215                 220

Thr Leu Cys Asp Gln Val Asp Ile Tyr Glu Phe Leu Pro Ser Lys Arg
225                 230                 235                 240

Lys Thr Asp Val Cys Tyr Tyr Gln Lys Phe Phe Asp Ser Ala Cys
                245                 250                 255

Thr Met Gly Ala Tyr His Pro Leu Leu Tyr Glu Lys Asn Leu Val Lys
                260                 265                 270

His Leu Asn Gln Gly Thr Asp Glu Asp Ile Tyr Leu Leu Gly Lys Ala
                275                 280                 285

Thr Leu Pro Gly Phe Arg Thr Ile His Cys
    290                 295
```

<210> SEQ ID NO 6
<211> LENGTH: 1003
<212> TYPE: DNA
<213> ORGANISM: Artificial Sequence
<220> FEATURE:
<223> OTHER INFORMATION: Expression construct Epo-AP-delta108 ST6
      (109-406)
<220> FEATURE:
<221> NAME/KEY: CDS
<222> LOCATION: (8)..(997)
<223> OTHER INFORMATION: open reading frame

<400> SEQUENCE: 6

```
gtcgacc atg ggc gtg cac gaa tgt cct gcc tgg ctg tgg ctg ctg ctg        49
        Met Gly Val His Glu Cys Pro Ala Trp Leu Trp Leu Leu Leu
        1               5                   10 agc ctg ctg tct ctg cct ctg gga ctg cct gtg ctg ggc gcc cct cct        97
Ser Leu Leu Ser Leu Pro Leu Gly Leu Pro Val Leu Gly Ala Pro Pro
15                  20                  25                  30 aga ctg cag aag atc tgg aag aac tac ctg agc atg aac aag tac aag       145
Arg Leu Gln Lys Ile Trp Lys Asn Tyr Leu Ser Met Asn Lys Tyr Lys
                35                  40                  45 gtg tcc tac aag ggc cct ggc cct ggc atc aag ttt agc gcc gag gcc       193
Val Ser Tyr Lys Gly Pro Gly Pro Gly Ile Lys Phe Ser Ala Glu Ala
            50                  55                  60 ctg aga tgc cac ctg agg gat cac gtg aac gtg tcc atg gtg gaa gtg       241
Leu Arg Cys His Leu Arg Asp His Val Asn Val Ser Met Val Glu Val
        65                  70                  75 acc gac ttc cca ttc aac acc agc gag tgg gag ggc tac ctg ccc aaa       289
Thr Asp Phe Pro Phe Asn Thr Ser Glu Trp Glu Gly Tyr Leu Pro Lys
80                  85                  90 gag agc atc cgg acc aaa gcc ggc cct tgg gga aga tgt gcc gtg gtg       337
Glu Ser Ile Arg Thr Lys Ala Gly Pro Trp Gly Arg Cys Ala Val Val
95                  100                 105                 110 tct agc gcc ggc agc ctg aag agt agc cag ctg ggc aga gag atc gac       385
Ser Ser Ala Gly Ser Leu Lys Ser Ser Gln Leu Gly Arg Glu Ile Asp
                115                 120                 125
```

```
gac cac gac gcc gtg ctg cgg ttc aat ggc gct ccc acc gcc aac ttc      433
Asp His Asp Ala Val Leu Arg Phe Asn Gly Ala Pro Thr Ala Asn Phe
            130                 135                 140 cag cag gac gtg ggc acc aag acc acc atc cgg ctg atg aac tcc cag      481
Gln Gln Asp Val Gly Thr Lys Thr Thr Ile Arg Leu Met Asn Ser Gln
        145                 150                 155 ctc gtg aca acc gag aag cgg ttc ctg aag gac agc ctg tac aac gag      529
Leu Val Thr Thr Glu Lys Arg Phe Leu Lys Asp Ser Leu Tyr Asn Glu
    160                 165                 170 ggc atc ctg atc gtg tgg gac ccc agc gtg tac cac agc gac atc ccc      577
Gly Ile Leu Ile Val Trp Asp Pro Ser Val Tyr His Ser Asp Ile Pro
175                 180                 185                 190 aag tgg tat cag aac ccc gac tac aac ttc ttc aac aac tac aag acc      625
Lys Trp Tyr Gln Asn Pro Asp Tyr Asn Phe Phe Asn Asn Tyr Lys Thr
                195                 200                 205 tac cgg aag ctg cac ccc aac cag ccc ttc tac atc ctg aag ccc cag      673
Tyr Arg Lys Leu His Pro Asn Gln Pro Phe Tyr Ile Leu Lys Pro Gln
            210                 215                 220 atg ccc tgg gag ctg tgg gac att ctg cag gaa atc agc ccc gaa gag      721
Met Pro Trp Glu Leu Trp Asp Ile Leu Gln Glu Ile Ser Pro Glu Glu
        225                 230                 235 atc cag ccc aac ccc cct agc tct ggc atg ctg ggc atc att atc atg      769
Ile Gln Pro Asn Pro Pro Ser Ser Gly Met Leu Gly Ile Ile Ile Met
    240                 245                 250 atg acc ctg tgc gac cag gtg gac atc tac gag ttt ctg ccc tcc aag      817
Met Thr Leu Cys Asp Gln Val Asp Ile Tyr Glu Phe Leu Pro Ser Lys
255                 260                 265                 270 aga aag acc gac gtg tgc tac tac tac cag aag ttc ttc gac agc gcc      865
Arg Lys Thr Asp Val Cys Tyr Tyr Tyr Gln Lys Phe Phe Asp Ser Ala
                275                 280                 285 tgc acc atg gga gcc tac cac cct ctg ctg tac gag aag aac ctc gtg      913
Cys Thr Met Gly Ala Tyr His Pro Leu Leu Tyr Glu Lys Asn Leu Val
            290                 295                 300 aag cac ctg aac cag ggc acc gac gag gat atc tac ctg ctg ggc aag      961
Lys His Leu Asn Gln Gly Thr Asp Glu Asp Ile Tyr Leu Leu Gly Lys
        305                 310                 315 gcc acc ctg ccc ggc ttc aga acc atc cac tgc tga ggatcc             1003
Ala Thr Leu Pro Gly Phe Arg Thr Ile His Cys
    320                 325
```

<210> SEQ ID NO 7
<211> LENGTH: 329
<212> TYPE: PRT
<213> ORGANISM: Artificial Sequence
<220> FEATURE:
<223> OTHER INFORMATION: Synthetic Construct

<400> SEQUENCE: 7

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Gln Lys Ile Trp Lys Asn Tyr Leu Ser Met Asn Lys Tyr Lys Val Ser
            35                  40                  45

Tyr Lys Gly Pro Gly Pro Gly Ile Lys Phe Ser Ala Glu Ala Leu Arg
        50                  55                  60

Cys His Leu Arg Asp His Val Asn Val Ser Met Val Glu Val Thr Asp
65                  70                  75                  80

Phe Pro Phe Asn Thr Ser Glu Trp Glu Gly Tyr Leu Pro Lys Glu Ser
```

```
                      85                  90                  95
Ile Arg Thr Lys Ala Gly Pro Trp Gly Arg Cys Ala Val Val Ser Ser
            100                 105                 110

Ala Gly Ser Leu Lys Ser Ser Gln Leu Gly Arg Glu Ile Asp Asp His
            115                 120                 125

Asp Ala Val Leu Arg Phe Asn Gly Ala Pro Thr Ala Asn Phe Gln Gln
            130                 135                 140

Asp Val Gly Thr Lys Thr Thr Ile Arg Leu Met Asn Ser Gln Leu Val
145                 150                 155                 160

Thr Thr Glu Lys Arg Phe Leu Lys Asp Ser Leu Tyr Asn Glu Gly Ile
            165                 170                 175

Leu Ile Val Trp Asp Pro Ser Val Tyr His Ser Asp Ile Pro Lys Trp
            180                 185                 190

Tyr Gln Asn Pro Asp Tyr Asn Phe Phe Asn Asn Tyr Lys Thr Tyr Arg
            195                 200                 205

Lys Leu His Pro Asn Gln Pro Phe Tyr Ile Leu Lys Pro Gln Met Pro
            210                 215                 220

Trp Glu Leu Trp Asp Ile Leu Gln Glu Ile Ser Pro Glu Glu Ile Gln
225                 230                 235                 240

Pro Asn Pro Pro Ser Ser Gly Met Leu Gly Ile Ile Ile Met Met Thr
            245                 250                 255

Leu Cys Asp Gln Val Asp Ile Tyr Glu Phe Leu Pro Ser Lys Arg Lys
            260                 265                 270

Thr Asp Val Cys Tyr Tyr Tyr Gln Lys Phe Phe Asp Ser Ala Cys Thr
            275                 280                 285

Met Gly Ala Tyr His Pro Leu Leu Tyr Glu Lys Asn Leu Val Lys His
            290                 295                 300

Leu Asn Gln Gly Thr Asp Glu Asp Ile Tyr Leu Leu Gly Lys Ala Thr
305                 310                 315                 320

Leu Pro Gly Phe Arg Thr Ile His Cys
            325
```